United States Patent
Teitelbaum

(10) Patent No.: US 8,668,903 B2
(45) Date of Patent: Mar. 11, 2014

(54) BIOLOGIC FEMALE CONTRACEPTIVES

(76) Inventor: Rachel Teitelbaum, Beit Shemesh (IL)

( * ) Notice: Subject to any disclaimer, the term of this patent is extended or adjusted under 35 U.S.C. 154(b) by 0 days.

(21) Appl. No.: 13/256,690

(22) PCT Filed: May 4, 2011

(86) PCT No.: PCT/IL2011/000352
§ 371 (c)(1),
(2), (4) Date: Sep. 15, 2011

(87) PCT Pub. No.: WO2011/138776
PCT Pub. Date: Nov. 10, 2011

(65) Prior Publication Data
US 2013/0045184 A1    Feb. 21, 2013

Related U.S. Application Data

(60) Provisional application No. 61/331,892, filed on May 6, 2010.

(30) Foreign Application Priority Data

Oct. 19, 2010   (IL) .......................................... 208820

(51) Int. Cl.
*A01N 63/00*   (2006.01)
*C12N 1/20*   (2006.01)
(52) U.S. Cl.
USPC ................... 424/93.1; 435/252.3; 435/252.9
(58) Field of Classification Search
None
See application file for complete search history.

(56) References Cited

U.S. PATENT DOCUMENTS

2005/0003510 A1*   1/2005   Chang et al. ................ 435/252.3

OTHER PUBLICATIONS

Yao et al (Methods vol. 38, pp. 124-132, 2006).*
Saito et al (Arch. Androl. vol. 20, No. 1, pp. 87-99, 1988).*
Naz et al (J. Reprod. Immunol. vol. 83 (1-2) pp. 145-150, 2009).*
Lefevre et al (Mol. Hum. Reprod. vol. 3 (6) pp. 507-516, 1997).*
Zhu et al (PNAS vol. 94 (9) pp. 4704-4709, 1997).*
Norton et al (Human Reproduction vol. 16 (9) pp. 1854-1860, 2001).*
Barborietti, A. et. al. Fertil. Steril. Jun. 30, 2011;95(8):2485-8.
Casari E. et. al. New Microbiologica, (2010) 33, 69-76.
Michael S. Donnenberg and B. Brett Finlay Trends in Microbiology, vol. 21, Issus 7, 317-319, Jul. 1, 2013.
Gioacchini G. et. al. Reproduction Dec. 2010;140(6):953-9.
Pelzer E.S. et. al. PLOS ONE (2013) vol. 8: e59062, 1-10.
Reid, G. et. al., Am J Obstet Gynecol (2003) vol. 189, No. 4, 1202-1208.
Reid, J, et. al. American Journal of Reproductive Immunology 69 (2013) 558-566.
Srinivasan S. et. al PLoS ONE (2012) 7: e37818, 1-15.

* cited by examiner

*Primary Examiner* — Albert Navarro

(57) ABSTRACT

This invention provides, inter alia, commensal organisms engineered to express antibody fragments, which inhibit sperm motility or fertilization and compositions comprising the same. The present invention provides for the use of the engineered commensal organisms or compositions comprising the same as effective contraceptive means in females.

16 Claims, 9 Drawing Sheets

```
Forward Frame 1:

1    M   A   E   V   Q   L   L   E   S   G   G   G   L   V   Q   P   G   G   S   L
1    ATGGCCGAGGTGCAGCTGTTGGAGTCTGGGGGAGGCTTGGTACAGCCTGGGGGGTCCCTG

21   R   L   S   C   A   A   S   G   F   T   F   S   D   H   D   M   H   W   V   R
61   AGACTCTCCTGTGCAGCCTCTGGATTCACCTTCAGTGACCACGACATGCACTGGGTCCGC

41   Q   A   P   G   K   G   L   E   W   V   S   G   I   S   W   K   S   D   S   M
121  CAGGCTCCAGGCAAGGGGCTGGAGTGGGTCTCAGGTATCAGTTGGAAAAGTGACAGTATG

61   A   Y   R   D   S   V   K   G   R   F   T   I   S   R   D   N   S   K   N   T
181  CCTATAGGGACTCTGTGAAGGGCCGATTCACCATCTCCAGAGACAATTCCAAGAACACG

81   L   Y   L   Q   M   N   S   L   R   A   E   D   T   A   V   Y   Y   C   A   R
241  CTGTATCTGCAAATGAACAGCCTGAGAGCCGAGGACACGGCCGTATATTACTGTGCGAGA

101  D   Q   E   H   F   D   F   D   Y   W   G   Q   G   T   L   V   T   V   S   S
301  GATCAGGAGCACTTCGACTTTGACTACTGGGGCCAGGGCACCCTGGTCACAGTCTCTTCA

121  G   S   A   G   G   G   G   S   G   G   G   G   S   G   G   G   G   S   D   I
361  GGCTCAGCAGGAGGAGGAGGATCCGGTGGTGGTGGTTCTGGCGGCGGCGGCTCCGATATC

141  V   L   T   Q   P   P   S   A   S   G   T   P   G   Q   R   V   T   I   S   C
421  GTGCTGACTCAGCCACCCTCAGCGTCTGGGACCCCCGGGCAGAGGGTCACCATCTCTTGC

161  S   G   S   S   S   N   L   G   S   N   T   V   N   W   Y   Q   Q   L   P   G
481  TCTGGAAGCAGCTCCAACCTCGGAAGTAATACTGTAAACTGGTACCAGCAGCTCCCAGGA

181  K   A   P   K   L   L   I   Y   D   N   N   Q   R   P   S   G   V   P   D   R
541  AAAGCTCCCAAACTCCTCATTTATGACAATAATCAACGACCCTCAGGGGTCCCTGACCGG

201  F   S   G   S   K   S   G   T   S   A   S   L   A   I   S   G   L   R   S   E
601  TTCTCTGGCTCCAAGTCTGGCACCTCAGCCTCCCTGGCCATCAGTGGGCTGCGGTCCGAG

221  D   E   A   D   Y   Y   C   A   A   W   D   D   S   L   S   G   L   V   F   G
661  GATGAGGCTGATTATTACTGTGCAGCATGGGATGACAGCCTGAGTGGGCTGGTGTTCGGG

241  T   G   T   K   L   T   V   L
721  ACCGGGACCAAACTCACTGTGCTG
```

Figure 5A

VH                                CDR1
EVQLLESGGGLVQPGGSLRLSCAASGFTFS  DHDMH  WVRQAPGKGLEWVS
     CDR2
GISWKSDSMAYRDSVKG  RFTISRDNSKNTLYLQMNSLRAEDTAVYYCAR
  CDR3
DQEHFDFDY  WGQGTLVTVSS
V-Lambda                    CDR1
DIVLTQPPSASGTPGQRVTISC  SGSSSNLGSNTVN  WYQQLPGKAPKLLIY
 CDR2                                              CDR3
DNNQRPS  GVPDRFSGSKSGTSASLAISGLRSEDEADYYC  AAWDDSLSGLV
FGTGTKLTVL
Figure 5B
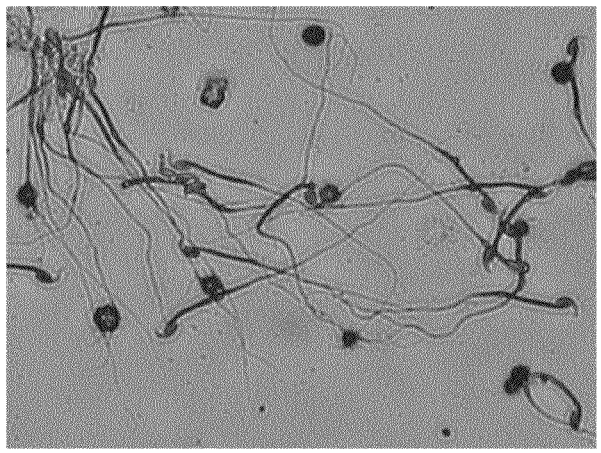
Figure 6A
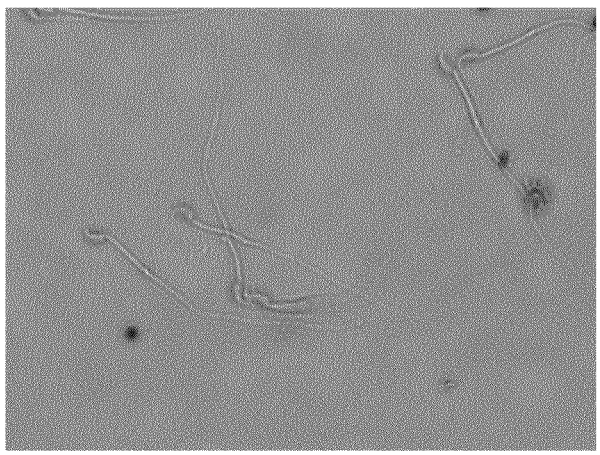
Figure 6B

SEQUENCE LISTING

```
<160> NUMBER OF SEQ ID NOS: 10

<210> SEQ ID NO 1
<211> LENGTH: 35
<212> TYPE: PRT
<213> ORGANISM: Homo sapiens

<400> SEQUENCE: 1

Ala Cys Gly Val Ser Arg Pro Val Ile Ala Cys Ser Val Thr Ile Lys
1               5                   10                  15

Glu Gly Ser Gln Leu Lys Gln Gln Ile Gln Ser Ile Gln Gln Ser Ile
            20                  25                  30

Glu Arg Leu
        35

<210> SEQ ID NO 2
<211> LENGTH: 12
<212> TYPE: PRT
<213> ORGANISM: Homo sapiens

<400> SEQUENCE: 2

Tyr Leu Pro Val Gly Gly Leu Arg Arg Ile Gly Gly
1               5                   10
```

```
<210> SEQ ID NO 3
<211> LENGTH: 23
<212> TYPE: PRT
<213> ORGANISM: Lactobacillus amylovorus

<400> SEQUENCE: 3

Met Lys Lys Asn Leu Arg Ile Val Ser Ala Ala Ala Ala Leu Leu
1               5                   10                  15

Ala Val Ala Pro Val Ala Ala
            20

<210> SEQ ID NO 4
<211> LENGTH: 23
<212> TYPE: PRT
<213> ORGANISM: Lactobacillus crispatus

<400> SEQUENCE: 4

Met Lys Lys Asn Leu Arg Ile Val Ser Ala Ala Ala Ala Leu Leu
1               5                   10                  15

Ala Val Ala Thr Val Ser Ala
            20

<210> SEQ ID NO 5
<211> LENGTH: 238
<212> TYPE: PRT
<213> ORGANISM: Lactobacillus crispatus

<400> SEQUENCE: 5

Val Thr Arg Thr Ile Asn Val Val Asp Pro Ile Thr Gly Lys Ile Ser
1               5                   10                  15

Thr Ser Val Gln Thr Ala Lys Phe Thr Arg Glu Asp Lys Asn Ser Asn
            20                  25                  30

Ala Gly Tyr Thr Asp Pro Val Thr Gly Lys Thr Thr Met Asn Pro Trp
        35                  40                  45

Thr Pro Ala Lys Gln Gly Leu Arg Ala Val Asn Val Glu Gln Ile Lys
    50                  55                  60

Gly Tyr Val Ala Lys Val Asp Gly Asn Val Asp Ala Val Val Val Thr
65                  70                  75                  80

Pro Asp Ser Ala Asn Met Val Val Thr Ile Thr Tyr Gln Ala Asn Lys
                85                  90                  95

Pro Glu Gly Gln Asn Ile Thr Asn Lys Lys Asp Thr Val Pro Asp Pro
            100                 105                 110

Ala Asp Gly Ile Lys Asn Lys Asp Asp Leu Pro Asp Gly Thr Lys Tyr
        115                 120                 125

Thr Trp Lys Glu Val Pro Asp Val Asn Ser Val Gly Glu Lys Thr Gly
    130                 135                 140

Ile Val Thr Val Thr Phe Pro Asp Gly Thr Ser Val Asp Val Lys Val
145                 150                 155                 160

Thr Val Tyr Val Asp Pro Val Val Glu Ser Asn Arg Asp Thr Leu Ser
                165                 170                 175

Lys Glu Ala Asn Thr Gly Asn Thr Asn Val Ala Lys Ala Ala Thr Val
            180                 185                 190

Thr Ser Ser Lys Val Glu Ser Lys Thr Leu Pro Gln Thr Gly Ser
        195                 200                 205

Lys Thr Glu Gln Val Gly Ile Leu Gly Leu Ala Ile Ala Thr Val Gly
    210                 215                 220

Ser Leu Leu Gly Leu Gly Val Asn Arg Lys Lys Arg Gln Lys
225                 230                 235
```

<210> SEQ ID NO 6
<211> LENGTH: 235
<212> TYPE: PRT
<213> ORGANISM: Lactobacillus crispatus

<400> SEQUENCE: 6

```
Lys Lys Ala Glu Glu Val Lys Asn Asn Ser Asn Ala Thr Gln Lys Glu
1               5                   10                  15

Val Asp Asp Ala Thr Asn Asn Leu Lys Gln Ala Gln Asn Asp Leu Asp
            20                  25                  30

Gly Gln Thr Thr Asp Lys Ser Lys Leu Asp Glu Ala Ile Lys Ser Ala
        35                  40                  45

Asp Asp Thr Lys Ser Thr Asp Lys Tyr Asn Asn Ala Ser Asp Asp Thr
50                  55                  60

Lys Ser Lys Phe Asp Glu Ala Leu Lys Lys Ala Glu Glu Val Lys Asn
65                  70                  75                  80

Asn Ser Asn Ala Thr Gln Lys Glu Val Asp Ala Thr Lys Asn Leu
            85                  90                  95

Lys Gln Ala Gln Asn Asp Leu Asp Gly Gln Thr Thr Lys Asp Ala
        100                 105                 110

Ile Asn Asp Ala Ile Lys Asp Ala Asn Asn Ala Lys Gly Thr Asp Lys
        115                 120                 125

Tyr Asn Asn Ala Ser Asp Asp Thr Lys Ser Lys Phe Asp Asp Ala Leu
130                 135                 140

Lys Lys Ala Glu Asp Val Lys Asn Asp Ser Asn Ala Asn Gln Lys Glu
145                 150                 155                 160

Val Asp Asp Ala Thr Lys Asn Leu Lys Asn Thr Leu Asn Asn Leu Lys
            165                 170                 175

Gly Gln Pro Ala Lys Lys Ala Asn Leu Ile Ala Ser Lys Asp Asn Ala
        180                 185                 190

Lys Ile His Lys Gln Thr Leu Leu Pro Gln Thr Gly Thr Glu Thr Asn
        195                 200                 205

Pro Leu Thr Ala Ile Gly Ile Gly Leu Met Ala Leu Gly Ala Gly Ile
    210                 215                 220

Phe Ala Lys Lys Lys Arg Lys Asp Asp Glu Ala
225                 230                 235
```

<210> SEQ ID NO 7
<211> LENGTH: 744
<212> TYPE: DNA
<213> ORGANISM: Homo sapiens

<400> SEQUENCE: 7

```
atggccgagg tgcagctgtt ggagtctggg ggaggcttgg tacagcctgg ggggtccctg      60
agactctcct gtgcagcctc tggattcacc ttcagtgacc acgacatgca ctgggtccgc     120
caggctccag gcaaggggct ggagtgggtc tcaggtatca gttggaaaag tgacagtatg     180
gcctataggg actctgtgaa gggccgattc accatctcca gagacaattc caagaacacg     240
ctgtatctgc aaatgaacag cctgagagcc gaggacacgg ccgtatatta ctgtgcgaga     300
gatcaggagc acttcgactt tgactactgg ggccagggca ccctggtcac agtctcttca     360
ggctcagcag gaggaggagg atccggtggt ggtggttctg gcggcggcgg ctccgatatc     420
gtgctgactc agccaccctc agcgtctggg acccccgggc agagggtcac catctcttgc     480
tctggaagca gctccaacct cggaagtaat actgtaaact ggtaccagca gctcccagga     540
```

```
aaagctccca aactcctcat ttatgacaat aatcaacgac cctcaggggt ccctgaccgg    600
ttctctggct ccaagtctgg cacctcagcc tccctggcca tcagtgggct gcggtccgag    660
gatgaggctg attattactg tgcagcatgg gatgacagcc tgagtgggct ggtgttcggg    720
accgggacca aactcactgt gctg                                          744
```

<210> SEQ ID NO 8
<211> LENGTH: 248
<212> TYPE: PRT
<213> ORGANISM: Homo sapiens

<400> SEQUENCE: 8

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Asp His Asp Met His Trp Val Arg Gln Ala Pro Gly Lys Gly Leu Glu
        35                  40                  45

Trp Val Ser Gly Ile Ser Trp Lys Ser Asp Ser Met Ala Tyr Arg Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Gln Glu His Phe Asp Phe Asp Tyr Trp Gly Gln
            100                 105                 110

Gly Thr Leu Val Thr Val Ser Ser Gly Ser Ala Gly Gly Gly Gly Ser
        115                 120                 125

Gly Gly Gly Gly Ser Gly Gly Gly Ser Asp Ile Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Ser Ser Asn Leu Gly Ser Asn Thr Val Asn Trp Tyr Gln
                165                 170                 175

Gln Leu Pro Gly Lys Ala Pro Lys Leu Leu Ile Tyr Asp Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Ala Trp Asp Asp Ser Leu Ser Gly Leu Val Phe Gly
225                 230                 235                 240

Thr Gly Thr Lys Leu Thr Val Leu
                245
```

<210> SEQ ID NO 9
<211> LENGTH: 26
<212> TYPE: DNA
<213> ORGANISM: Artificial Sequence
<220> FEATURE:
<223> OTHER INFORMATION: Forward Primer

<400> SEQUENCE: 9

```
ccatgattac gccaagcttg ggagcc                                         26
```

<210> SEQ ID NO 10
<211> LENGTH: 21
<212> TYPE: DNA

-continued

```
<213> ORGANISM: Artificial Sequence
<220> FEATURE:
<223> OTHER INFORMATION: Primer

<400> SEQUENCE: 10
gaattcaacc ttcaaattgc c                                                    21
```

BIOLOGIC FEMALE CONTRACEPTIVES

CROSS-REFERENCE TO RELATED APPLICATIONS

This application is a 371 National Stage filing of PCT International Application Number PCT/IL2011/000352, filed May 4, 2011, which claims the benefit of U.S. Provisional Application Ser. No. 61/331,892, filed on May 6, 2010 and Israeli Application number 208820 filed Oct. 19, 2010 all of which are hereby incorporated by reference in their entirety.

FIELD OF THE INVENTION

This invention provides commensal organisms engineered to express antibody fragments, which inhibit sperm motility, fertilization or a combination thereof and compositions comprising the same. The present invention provides for the use of such engineered commensal organisms or compositions comprising the same as contraceptives.

BACKGROUND OF THE INVENTION

The development of new contraceptives is necessary to provide accessible birth control to all individuals, regardless of sociological, financial or education limitations.

While a number of different contraceptives are currently available, none are problem free. By far, the most commonly used contraceptive is an oral estrogen, progesterone, or combination thereof formulation, which while effective, nonetheless has been suggested to be proneoplastic, with prolonged use, and in some populations.

Barrier methods, such as the diaphragm, or intra-uterine device, exhibit dimished efficacy, and non-compliance with the former, and greater risk with pelvic inflammatory disease with use of the latter. Spermicides have also been used in this context, with less efficacy, and moreover, higher risk for sexually transmitted disease is associated with such use.

Thus, an easy to use, minimally invasive contraceptive, which is not associated with the above limitations is needed.

SUMMARY OF THE INVENTION

The invention provides, in one embodiment, a genetically engineered cell which produces an antibody fragment against a sperm antigen, and thereby can serve as a contraceptive.

In one embodiment, the invention provides an engineered commensal bacterium of the female genital tract, wherein the bacterium is engineered to express an antibody to sperm, or a fragment thereof, effective to prevent sperm motility, sperm-egg fusion or sperm penetration of the egg, or a combination thereof. In some embodiments, the antibody fragment is a single chain Fv molecule (scFv).

In some embodiments, the antibody fragment specific for a sperm antigen is human-derived or humanized. In some embodiments, the antibody fragment specifically interacts with an acrosome or plasma membrane localized antigen on the sperm or a fragment thereof. In some embodiments, the antibody fragment specifically interacts with a sperm neck region localized antigen or a fragment thereof. In some embodiments, the antibody fragment is secreted from the engineered bacterium, and in some embodiments, the antibody fragment is associated with or bound to the bacterial cell wall.

In some embodiments, the engineered bacterium is *Lactobacillus*, or in some embodiments *Lactococcus*. In some embodiments, the engineered bacterium is *Escherichia coli* Nissle 1917 strain. In some embodiments, the engineered bacterium is *S. gordonii*. In some embodiments, the engineered bacterium is *L. jensenii* or *L. crispatus*.

In some embodiments, the scFv specifically interacts with a peptide sharing at least 90% identity with SEQ ID NO: 1 or 2. In some embodiments, the scFv has a sequence sharing at least 90% identity with SEQ ID NO: 8. In some embodiments, the scFv is encoded by a polynucleotide having a sequence sharing at least 90% identity with SEQ ID NO: 7.

In some embodiments, the invention provides a composition comprising the engineered bacteria as herein described. In some embodiments, the composition is in the form of a vaginal suppository, cream or foam. In some embodiments, the contraceptive is associated with or incorporated on a vaginal ring.

In some embodiments, the invention provides a method of contraception, said method comprising the steps of contacting cells of the genital tract of a female subject with engineered bacteria as herein described in an amount sufficient to inhibit or prevent sperm motility, sperm-egg fusion or egg penetration in the female subject. In some embodiments, according to this aspect, the method comprises administering a composition comprising the engineered bacteria to the genital tract of a female subject in need thereof in an amount sufficient to inhibit or prevent.

In some embodiments, the invention provides a method of reducing the incidence of pregnancy in a female population, said method comprising the steps of contacting cells of the genital tract of a female subject with engineered bacteria as herein described in an amount sufficient to impair, inhibit or prevent sperm motility, sperm-egg fusion or egg penetration in the female subject, thereby reducing the incidence of pregnancy in a female and thereby reducing the incidence of pregnancy in a female population.

In some embodiments, the invention provides a method of reducing the incidence of fertilization in a female population, said method comprising the steps of contacting cells of the genital tract of a female subject with engineered bacteria as herein described in an amount sufficient to impair, inhibit or prevent sperm motility, sperm-egg fusion or egg penetration in the female subject, thereby reducing the incidence of fertilization occurrence in a female and thereby reducing the incidence of fertilization in a female population.

In some embodiments, the invention provides for the use of an engineered bacterium or a composition as herein described in the manufacture of a medicament for use in the reduction of the incidence of pregnancy in a female population. In some embodiments, the invention provides for the use of an engineered bacterium or a composition as herein described in the manufacture of a medicament for use in the reduction of the incidence of fertilization in a female population.

BRIEF DESCRIPTION OF THE FIGURES

FIG. 5A depicts the nucleic acid and amino acid sequence of J102, respectively (SEQ ID NO: 7-8). FIG. 5B depicts the respective domains within the J102 scFv.

FIG. 6 depicts specific binding of the J102 expressing *lactobacilli* to murine sperm, in vitro. FIG. 6A is a light micrograph showing significant binding of the *lactobacilli* expressing scFv to mouse sperm, with almost each sperm cell evaluated showing significant staining. FIG. 6B is a light micrograph of a J112 expressing *lactobacilli*, serving as a control, where no appreciable binding to murine sperm is evident.

FIG. 7 graphically depicts in vivo demonstration of the efficacy of J102 expressing *lactobacilli*.

DETAILED DESCRIPTION OF THE INVENTION

Figure 1:
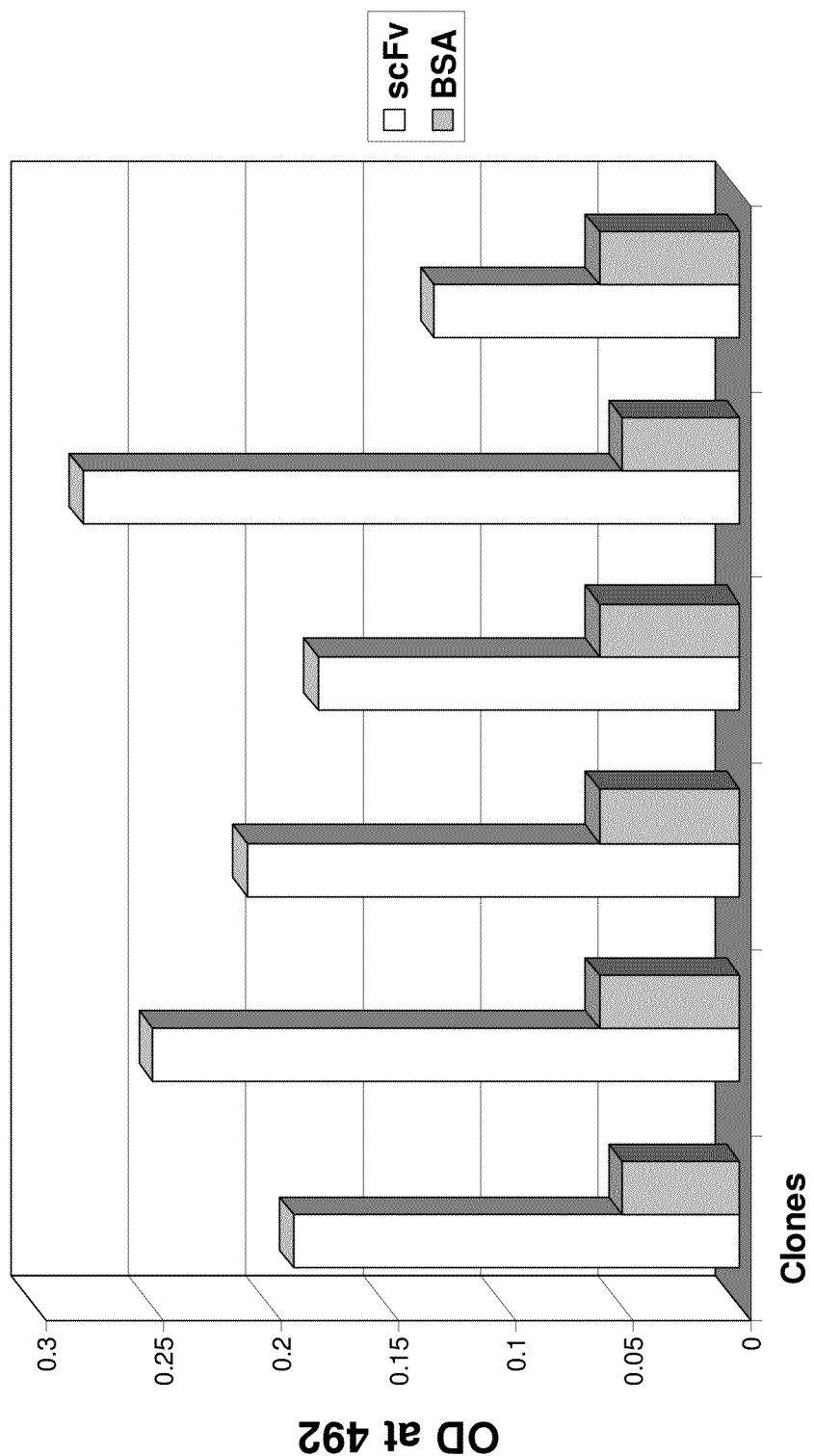
FIG. 1 graphically depicts the relative affinities of phage displayed scFvs isolated and cloned against sperm peptides determined by ELISA assay. Columns 1-3 represent binding of three scFvs to the sperm FA-1 derived peptide and columns 4-6 represent binding of three scFvs to the sperm YLP(12)-derived peptide. BSA served as a negative binding control.

This invention provides, in one embodiment, recombinant cells, including, in one embodiment, microorganisms and methods for utilizing same, for production of spermicidal compounds. The methods and cells, in one embodiment, provide an effective means of contraception.

In one embodiment, the recombinant cell is a commensal organism of the female reproductive tract. In one embodiment, the commensal organism is a bacterium.

In one embodiment, the recombinant cell is a non-mammalian cell, which persists in the mucosa of the female genital tract for a period of time sufficient to express a compound, which interferes with sperm motility, sperm-egg fusion or sperm penetration of the egg. In some embodiments, the compound, when expressed in the female genital tract of the treated subject by the commensal organism colonizing the same results in reduced fertility in the subject. In some embodiments, the compound, when expressed in the female genital tract of the treated subjects results in a reduced pregnancy rate in a population administered such commensal organism.

In one embodiment, the invention provides for an engineered commensal organism expressing a spermicidal compound, which organism is capable of colonizing the female reproductive tract or regions thereof.

In one embodiment, the cell is engineered to express a nucleic acid fragment that is capable of being expressed as a specific protein, including regulatory sequences preceding (5' non-coding sequences) and following (3' non-coding sequences) the coding sequence.

The genetically engineered bacteria may be engineered to be deficient in specific genes via any means as will be known to one skilled in the art, or the engineered organisms may be engineered to overexpress certain genes, by methods known in the art.

In one embodiment, a construct is introduced in the bacteria of this invention, such that it is possible to select for homologous recombination events in the bacterium for gene knock-out procedures. One of ordinary skill in the art can readily design a knock-out construct including both positive and negative selection genes for efficiently selecting transfected cells that underwent a homologous recombination event with the construct.

In another embodiment, changes in gene expression, activity and function, including, inter alia, enhanced, diminished, and abrogated gene expression may be accomplished using a genetic construct that integrates into the genome of the cell. In another embodiment, changes in gene expression, activity and function may be accomplished using a genetic construct that is extra-chromosomal, and in one embodiment, remains extra-chromosomal.

In one embodiment, the term construct or vector refers to nucleic acid vehicle containing a sequence of interest that has been subcloned within the vector.

To generate the vectors of the present invention, polynucleotides encoding sequences of interest can be ligated into an appropriate expression vector systems suitable for transducing/transforming prokaryotic cells and for directing the expression of recombinant products within the transduced/transformed cells. It will be appreciated that such appropriate vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter genes.

According to another embodiment, the vectors further comprise a regulatory element, such as a promoter for regulating expression of the isolated nucleic acid. Such promoters are known to be cis-acting sequence elements required for transcription as they serve to bind DNA dependent RNA polymerase, which transcribes sequences present downstream thereof. The vector may, in another embodiment, comprise an inducible promoter, or one that expresses the sequences of interest constitutively.

A vector according to the present invention, may further include an origin of replication, and may propagate in more than one species of prokaryotic cell, and in some embodiments, the vector may be constructed to facilitate its integration within the genome of an organism of choice. The vector, in other embodiments may be, for example, a plasmid, a bacmid, a phagemid or a phage, or any appropriate vector, as will be appreciated by the skilled artisan.

An example of such vector is described and utilized in the Examples section, hereinbelow. It will be understood by the skilled artisan, however, that the invention is not restricted to the use of any such vector, and that it is routine in the art to create new vectors, and/or modify existing vectors, for the goal of optimizing heterologous expression of the inserted or incorporated sequence, for which the vector serves as the genetic delivery/engineering vehicle.

Some examples of vectors suitable for use include: M. Posno et al., Appl Environ Microbiol. 1991 June; 57(6): 1822-1828; M Shimizu-Kadota, et. al., Appl Environ Microbiol. 1991 November; 57(11): 3292-3300; T. Duong, et. al., Microbial Biotechnology Volume 4, Issue 3, pages 357-367, May 2011; V V Aleshin et al., Mikrobiologiia Volume: 69, Issue: 1, Pages: 75-80; X. Liu et al., Antimicrobial agents and chemotherapy 2006, vol. 50, no 10, pp. 3250-3259; WO/2005/112567; Luca Vangelista et. al., Antimicrobial Agents and Chemotherapy, July 2010, p. 2994-3001, Vol. 54, No. 7; U.S. Pat. No. 7,179,458; U.S. Pat. No. 7,754,467; Caren J. Chancey, et. al., The Journal of Immunology, 2006, 176: 5627-5636; U.S. Pat. No. 5,733,540 and others.

Incorporation of desired nucleic acid sequences within cells can be accomplished through a number of methods well known in the art. Nucleic acid constructs can be utilized to stably or transiently transfect or transduce the cells.

There are a number of techniques known in the art for introducing vectors into cells of the present invention, such as, but not limited to: direct DNA uptake techniques, and phage, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged. It is to be understood that any of these methods may be utilized for introduction of the desired sequences into cells, for production of the cells of this invention, and for effecting the methods of this invention.

Electroporation has been used successfully for the transformation of various cells.

Bacterial conjugation, relying on the direct contact of donor and recipient cells, may also be used for the transfer of genes into bacteria. Bacterial conjugation processes may involve mixing together "donor" and "recipient" cells in close contact with one another. Conjugation occurs by formation of cytoplasmic connections between donor and recipient bacteria, with direct transfer of newly synthesized donor DNA into the recipient cells. The recipient in a conjugation accepts DNA through horizontal transfer from a donor bacterium. The donor in conjugative transfer may have a conjugative plasmid, conjugative transposon, or mobilizable plasmid.

In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1) Double-strand plasmid DNA is nicked at a specific site in oriT; 2) A single-strand DNA is released to the recipient through a pore or pilus structure; 3) A DNA relaxase enzyme cleaves the double-strand DNA at oriT and binds to a released 5' end (forming a relaxosome as the intermediate structure); and 4) Subsequently, a complex of auxiliary proteins assemble at oriT to facilitate the process of DNA transfer.

A "triparental" conjugation may also be required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

The term "recombinant" or "recombinantly altered" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" is a nucleic acid, generated recombinantly or synthetically, with a series of specified nucleic acid elements that permit transcription of a particular nucleic acid in a host cell. The expression cassette can be part of a plasmid, virus, or nucleic acid fragment. Typically, the expression vector includes a nucleic acid to be transcribed operably linked to a promoter.

In another embodiment, nucleic acids used in this invention comprise analogs of either RNA or DNA made from nucleotide analogs. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target, increased stability in the presence of nucleases and/or efficient gene silencing.

The nucleic acids used in this invention can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

In another embodiment, in vitro transposition may be conducted upon genomic DNA cloned into a vector, for example a cosmid, phage, plasmid, or BAC (bacterial artificial chromosome) vector. Similar high-density mutagenesis can be performed in non-naturally competent organisms using genomic DNA cloned into an allelic replacement vector (see for example, U.S. Pat. No. 6,207,384, which methods may be utilized to engineer the organism as herein described.

Appropriate bacterial host strains are selected for, e.g. their transformation ability, ability for heterologous protein expression, and/or mucosal surface. The bacterial host will be rendered competent for transformation using standard techniques, such as the rubidium chloride method or electroporation (see, e.g., Wei et al., J. Microbiol. Methods 21:97-109 (1995).

Transformation of a commensal, for example, *L. jensenii* by electroporation can be performed by modifying standard methods as described in, e.g., Luchansky et al. (J. Dairy Sci. 74: 3293-3302 (1991). Briefly, freshly inoculated *L. jensenii* are cultured in MRS broth (e.g., to 0.6-0.7 at $OD_{600}$ at 37° C. and 5% $CO_2$). The bacterial cells are harvested, washed and resuspended in a cold solution of sucrose and $MgCl_2$. Competent cells are then mixed with DNA and electroporated. Afterward, cells are allowed to recover prior to being plated on selective agar plate containing an antibiotic other selective agent. The engineered cells are then administered to the subject, for example, in a suppository, cream or foam formulation.

Optionally, antibiotic pretreatment can be used to pre-clear the mucosal surface of resident bacteria prior to introduction of the bacteria of the invention into the vagina (see, e.g., Freter et al., Infect. Immun., 39:686-703 (1983)). Antibiotics can be provided orally or can be applied directly to the vagina.

In some embodiments, the invention provides for a non-limiting method for selection of a bacterial strain for engineering in accordance with the methods of this invention, which strain is efficient in colonizing the mucosal surface to which the bacteria is applied which method may involve repetitively selecting for rapid colonizing bacteria on animal or human mucosal layers. For example, one applies a wild-type bacterial strain to a mucosal surface and repetitively isolates and in vitro cultures the bacteria, returning at each step to the mucosal surface. In some embodiments, according to this aspect, ultimately, a bacterium with an enhanced colonizing ability is obtained.

In another embodiment, the invention provides a non-limiting method for engineering a bacterial strain accordance with the methods of this invention, which strain is efficient in colonizing the mucosal surface to which the bacteria is applied may involve expression of fusion proteins on the surface of recombinant bacteria. The fusion protein consists of a host-binding domain linked to a polypeptide of interest. The host-binding domain will allow the bacteria to bind to certain determinants (protein or carbohydrate) on a selected host mucosal surface with high affinity, thus conferring the bacteria a survival advantage over the resident microflora.

Another embodied method for engineering bacterial strains of the invention involves induction of resident microflora to express a heterologous protein by introducing the gene via bacteriophage. A number of bacteriophage vectors have been developed for use in different bacteria. For example, a bacteriophage vector based on the temperate bacteriophage adh can be used (see, e.g., Raya et al., J. Bacteriol. 174:5584-5592 (1992) and Fremaux et al, Gene 125:61-66 (1993)). This vector undergoes site-specific integration into the host chromosome at defined phage (attP) and bacterial (attB) attachment sites. Similarly, *Lactobacillus*-specific bacteriophage can be used to transduce vectors or other polynucleotides into the *Lactobacillus* chromosome. *Lactobacillus*-specific phage include mv4 (Auvray et al., J. Bacteriol., 179:1837-1845 (1997)), adh (Fremaux et al., Gene 126:61-66 (1993)), gle (Kakikawa et al., Gene 175:157-165 (1996), and those belonging to Bradley's groups A or B in vaginal *lactobacillus* isolates (Kilic et al., Clin. Diagn. Lab. Immunol. 8:31-39 (2001)).

Certain agents that do not irritate mucosal epithelial cells may also be added to a unit dose of the bacteria to aid in colonization. Many bacteria on mucosal surfaces secrete capsular materials that coalesce to form a biofilm that covers the entire mucosal surface. It may be beneficial to add an enzyme that digests this biofilm material to promote penetration of the engineered bacteria into the biofilm for more successful colonization. The enzymes include DNAses, peptidases, collagenases, hyaluronidases, and other carbohydrate degrading enzymes. Antibiotics to which the engineered bacteria itself is not susceptible may also be added to decrease the number of resident bacteria on the mucosal surface in order to facilitate effective colonization of the engineered bacteria.

Expression of the heterologous polynucleotides or polypeptides can be constitutive (e.g., using P59 (van der Vossen et al., Appl. Environ. Microbiol. 58:3142-3149 (1992)) or P23 (Elliot et al., Cell 36:211-219 (1984)) promoters). Alternatively, expression can be under the control of an inducible promoter. For example, the Bacillus amylase (Weickert et al., J. Bacteriol. 171:3656-66 (1989)) or xylose (Kim et al. Gene 181:71-76 (1996)) promoters as well as the *Lactococcus nisin* promoter (Eichenbaum et al., Appl. Environ. Microbiol. 64:2763-2769 (1998)) can be used to drive inducible expression. In addition, acid or alkaline-induced promoters can be used. For example, promoters that are active under the relatively acidic conditions of the vagina (e.g., those described in U.S. Pat. No. 6,242,194) can be used. Alternatively, promoters can be used that are induced upon changes in the vagina in response to semen. For example, alkaline-induced promoters are used to induce expression in response to the increased alkaline conditions of the vagina resulting from the introduction of semen.

A variety of signal and anchor sequences are known to direct expression of polypeptides to the membrane, extracellular space or the cell wall (e.g., by covalent attachment to peptidoglycan). Exemplary signal sequences include the signal sequence from α-Amylase of *L. amylovorus* (Giraud & Cuny, Gene 198:149-157 (1997)) or the signal sequence from the S-layer gene (cbsA) of *L. crispatus* (e.g., MKKNL-RIVSAAAAALLAVAPVAA (SEQ ID NO:3) or MKKNL-RIVSAAAAALLAVATVSA (SEQ ID NO:4)). Signal sequences are typically located at the amino-terminus of a polypeptide.

Anchor sequences are typically located at the carboxyl terminus of an encoded protein sequence. Anchor sequences include, e.g., a cell wall associated sequence; the sequence LPQ(S/A/T)(G/A), where residues in parentheses indicate different options at that position; and a hydrophobic sequence, and, optionally, a charged sequence. In some embodiments, the anchoring sequence comprises VTRTINVVDPITGKISTSVQTAKFTREDKNSNAGYT- DPVTGKTTMNPWTPAKQGLRA VNVEQIKGY-
VAKVDGNVDAVVVTPDSANMVVTITYQANKPEG-
QNITNKKDTVPDP ADGIKNKDDLPDGTKYTWKEVP-
DVNSVGEKTGIVTVTFPDGTSVDVKVTVYVDPVV
ESNRDTLSKEANTGNTNVAKAATVTSSKVESKKTLP-
QTGSKTEQVGILGLAIATVGS LLGLGVNRKKRQK
(SEQ ID NO:5); or KKAEEVKNNSNATQKEVDDAT-
NNLKQAQNDLDGQTTDKSKLDEAIKSADDTKSTD
KYNNASDDTKSKFDEALKKAEEVKNNSNATQKEVD-
DATKNLKQAQNDLDGQTTN KDAINDAIKDANNA-
KGTDKYNNASDDTKSKFDDALKKAEDVKNDSNA-
NQKEVDD ATKNLKNTLNNLKGQPAKKANLIASKD-
NAKIHKQTLLPQTGTETNPLTAIGIGLMAL GAGI-
FAKKKRKDDEA (SEQ ID NO:6), or sequences substantially identical to SEQ ID NO:5 or SEQ ID NO:6.

Correct localization and folding of a polypeptide can be determined using standard methods. For example, cell wall enriched fractions of *Lactobacillus* can be obtained by suspending the bacteria in a buffered, solution (e.g., 25% sucrose, 1 mM EDTA, 10 mM Tris-HCl, pH 8.0) followed by treatment with cell wall degrading enzymes (e.g., lysozyme and mutanolysin) and then separating out the resulting protoplasts by differential centrifugation (Piard et al., J. Bacteriol. 179:3068-3072 (1997)). Fractions can then be screened by Western blotting to confirm expression within the cell wall.

Folding and biological activity of an expressed polypeptide can also be determined using standard methods. For example, ELISA assays using antibodies specific for the natively folded polypeptide can be used to confirm folding and three-dimensional structure of the polypeptide. Biological activity assays will of course vary depending on the activity of the polypeptide. For example, for polypeptides that bind to the sperm, the expressed polypeptide can be tested using standard binding assays.

When synthesizing a gene for improved expression in a host cell, it is desirable to design the gene such that its frequency of codon usage approaches the frequency of preferred codon usage of the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons.

The polynucleotide sequence encoding a particular polypeptide can be altered to coincide with the codon usage of a particular host. For example, the codon usage of *Lactobacillus* can be used to derive a polynucleotide that encodes a polypeptide of the invention and comprises preferred *Lactobacillus* codons. The frequency of preferred codon usage exhibited by a host cell can be calculated by averaging the frequency of preferred codon usage in a large number of genes expressed by the host cell. This analysis is preferably limited to genes that are highly expressed by the host cell. Pouwels & Leunissen (Nucleic Acids Res. 22:929-936 (1994)), for example, provides the frequency of codon usage by highly expressed genes exhibited by various *Lactobacillus* species. Codon-usage tables are also available via the internet.

In another embodiment, the vector contemplated by this invention further comprises an insertion of a heterologous nucleic acid sequence encoding a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art.

A variety of Aequorea-related GFPs having useful excitation and emission spectra have been engineered by modifying the amino acid sequence of a naturally occurring GFP from *Aequorea victoria* (Prasher et al., 1992, Gene, 111: 229-233; Heim et al., 1994, Proc. Natl. Acad. Sci. U.S.A., 91: 12501-12504; PCT/US95/14692).

Transfer of nucleic acids having sequences encoding spermicidal compounds into heterologous organisms results in expression, in one embodiment.

Methods for the detection of the expressed product are well known in the art, and may comprise, in one embodiment, Northern Blot, PCR, HPLC, Mass Spectroscopy, ELISA, RIA or Western blot analysis [see "Cell Biology: A Laboratory Handbook", Volumes I-III Cellis, J. E., ed. (1994); "Current Protocols in Immunology" Volumes I-III Coligan J. E., ed. (1994); Stites et al. (eds)].

In some embodiments, antibiotic resistance cassettes may be introduced in the organisms as herein described as markers for confirming expression of the introduced construct. In some embodiments, antibiotic susceptibility cassettes will be introduced in the organisms, as a safety protocol for constructs introduced into subjects, and in some embodiments, for abrogation of the contraceptive effect, to facilitate a safe means for conception, e.g. by the subject injesting as short course of antibiotic therapy, which eradicates the biologic contraceptive.

This invention provides, in some embodiments, an engineered cell expressing a spermicidal compound. In one embodiment, the spermicidal compound may comprise an antibody to sperm, or a fragment thereof, effective to prevent sperm motility, sperm-egg fusion or sperm penetration of the egg, or a combination thereof.

Antibodies exist, e.g., as intact immunoglobulins or as a number of well characterized fragments. In some embodiments, scFv fragments are contemplated as part of the engineered organisms, compositions, kits and for use in accordance with the methods of this invention. In some embodiments, other contemplated framents include an F(ab')2, an Fab' monomer. The Fab' monomer is essentially an Fab with part of the hinge region (see, Paul (Ed.) Fundamental Immunology, Third Edition, Raven Press, NY (1993)) and others. While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv (scFv)).

Embodied methods of preparation of such cells are described herein, however the skilled artisan will appreciate that any spermicidal compound, or combinations of compounds may be produced recombinantly in a commmensal organism.

In some embodiments, antibody fragments, which are spermicidal or otherwise inhibit sperm motility or sperm-egg fusion capability or egg penetration by sperm in various animal species are utilized. For example, and in some embodiments, the antibody fragment, for example scFv, specifically interacts with a highly conserved sperm specific epitope, which is conserved in animal species and humans, such that in vivo efficacy testing may be conducted in animal models, and validation of the same antibody fragment, for example human scFv or a humanized version thereof may be undertaken in human clinical trials.

In some embodiments, such antibodies/antibody fragments may be generated as exemplified herein, or as described in Xu, et al. Arch Androl. 1994 September-October; 33(2):141-4; Clarke et al., Arch Androl. 1995 July-August; 35(1):21-7; WO0107083A1; U.S. Pat. Nos. 5,830,472, 5,753,231, 5,227,160 or by any appropriate method, as will be appreciated by one skilled in the art. Engineering a commensal organism to express such a compound may be accomplished by any means, as well, for example as described in PNAS 102:11993-11998 (2003).

Completely human antibodies/antibody fragments are particularly desirable for applications in contraception in human females. Human antibodies/antibody fragments can be made by a variety of methods known in the art including phage display methods described herein using antibodies/antibody fragments libraries derived from human immunoglobulin sequences. See U.S. Pat. Nos. 4,444,887 and 4,710,111; and WO 98/46645; WO 99/50433; WO 98/24893; WO 98/16654; WO 96/34096; WO 96/33735; and WO 91/10741, each of which is incorporated herein by reference in its entirety and including the Examples provided hereinbelow.

It is to be understood that any reference cited herein is to be considered to be incorporated in entirety by reference thereto.

Human antibodies or antibody fragments, for example scFv can also be produced using transgenic mice which are incapable of expressing functional endogenous immunoglobulins, but which can express human immunoglobulin genes. For an overview of this technology for producing human antibodies, see Lonberg and Huszar, 1995. For a detailed discussion of this technology for producing human antibodies and human monoclonal antibodies and protocols for producing such antibodies and fragments thereof, see, e.g., WO 98/24893; WO 92/01047; WO 96/34096; WO 96/33735; EP 0598877; U.S. Pat. Nos. 5,413,923; 5,625,126; 5,633,425; 5,569,825; 5,661,016; 5,545,806; 5,814,318; 5,885,793; 5,916,771; and 5,939,598; which are incorporated by reference herein in their entireties. In addition, companies such as Abgenix, Inc. (Freemont, Calif.). Kirin, Inc. (Japan), Medarex (NJ) and Genpharm (San Jose, Calif.) can be engaged to provide human antibodies directed against a selected antigen using technology similar to that described above.

The antibodies of the invention may also be modified by the methods and coupling agents described by Davis et al. (U.S. Pat. No. 4,179,337) in order to produce antibody fragments, which induce substantially no immunogenic response.

In some embodiments, the invention provides a composition comprising the engineered bacteria as herein described.

In some embodiments, the composition may comprise engineered bacteria as herein described, where the composition comprises bacteria which express different heterologous anti-sperm agents, and yet are contained within the same composition as part of the unit dose administered. In some embodiments, such bacteria expressing different heterologous anti-sperm agents may vary in terms of the specificity for a particular antigen or epitope, or may vary in terms of the antigen or epitope to which the fragment binds, or may vary in terms of avidity for the epitope, or vary in terms of the isotype from which it is derived, or combinations thereof.

In some embodiments, such composition may also comprise different bacterial strains expressing the same or different heterologous anti-sperm agents, which are contained within the same composition as part of the unit dose administered, as well.

In some embodiments, the composition is in the form of a vaginal suppository, liquid, spray, foam, cream, mousse, or any appropriate vehicle for vaginal delivery.

In some embodiments, the engineered bacteria or compositions comprising the same are applied to or incorporated within a vaginal ring, which is then administered to a female subject. In some embodiments, the invention contemplates a condom containing an engineered bacteria or compositions comprising the same applied to the outer surface of the condom and preserved such that the wearer of the condom may transfer the engineered bacteria to his female partner during intercourse.

In some embodiments, the term "comprise" or grammatical forms thereof, refers to the inclusion of the indicated active agent, such as the engineered commensal of this invention or phage as herein described, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, i.e. the engineered commensal organism as herein described however, other agents/components/compounds may be included which are for stabilizing, preserving, etc. the formulation, but are not involved directly in the contraceptive effect. In some embodiments, the term "consisting essentially of" may refer to components, which exert a contraceptive effect via a mechanism distinct from that of the engineered commensal organism, which enhance the contraceptive efficacy or prolong the contraceptive efficacy or both. In some embodiments, the term "consisting essentially of" may refer to components which facilitate the release of the engineered commensal organism, for example, by enhancing its release from the suppository formulation or other formulation, promote effective colonization, promote uniform colonization, and other desirable effects, which facilitate the activity of the engineered commensal organism, yet are not components of the engineered commensal organism. In some embodiments, such agents may include agents which induce expression of the encoded anti-sperm agent, or in some embodiments, enhance expression of the encoded anti-sperm agent. In some embodiments, the term "consisting" refers to a composition, which contains the active ingredient and a pharmaceutically acceptable carrier or excipient.

Delivery of engineered bacteria to a desired mucosal surface depends on the accessibility of the area and the local conditions. For example, engineered bacteria may be placed in a saline solution, cream, suppository or in a foam for delivery onto the vaginal mucosa. Foams can include, e.g., one or more hydrophobically modified polysaccharides such as cellulosics and chitosans. Cellulosics include, for example, hydroxyethyl cellulose, hydroxypropyl cellulose, methyl cellulose, hydroxypropylmethyl cellulose, hydroxyethyl methyl cellulose, and the like. Chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, and the like. Foam can also include other components such as water, ethyl alcohol, isopropyl alcohol, glycerin, glycerol, propylene glycol, and sorbitol. Spermicides are optionally included in the bacterial composition. Further examples of foams and foam delivery vehicles are described in, e.g., U.S. Pat. Nos. 5,595,980 and 4,922,928.

In some embodiments, the bacteria can be delivered as a suppository or pessary. See, e.g., U.S. Pat. No. 4,322,399. In some embodiments, the bacteria of the invention are prepared in a preservation matrix such as described in U.S. Pat. No. 6,468,526 and are delivered in a dissolvable element made of dissolvable polymer material and/or complex carbohydrate material selected for dissolving properties, such that it remains in substantially solid form before use, and dissolves due to human body temperatures and moisture during use to release the agent material in a desired timed release and dosage. See, e.g., U.S. Pat. No. 5,529,782. The bacteria can also be delivered in a sponge delivery vehicle such as described in U.S. Pat. No. 4,693,705.

In some embodiments, applications of engineered bacteria to a mucosal surface will need to be repeated on a regular basis; optimal dosing intervals are routine to determine, but will vary with different mucosal environments and bacterial strain. The dosing intervals, in some embodiments, can vary from once daily to once every 2-4 weeks, or longer. In some embodiments, administration will follow a female menstrual cycle, such that administration will follow the cessation or approximate cessation of menstruction to optimize colonization prior to ovulation in the female being treated thereby.

In some embodiments where bacteriophage are introduced to transform native *Lactobacillus*, the nucleic acid of the selected bacteriophage may be manipulated such that the heterologous gene(s) replaces the genes coding for bacteriophage coat proteins, rendering the bacteriophage replication-defective. Adding these recombinant DNA molecules into cell lysates containing functional bacteriophage proteins will lead to assembly of functional bacteriophage particles carrying the heterologous gene(s). These replication-defective bacteriophage particles can then be introduced onto a desired mucosal surface to infect selected floral bacteria. The typical dosage would be $10^8$ to $10^{12}$ PFU/ml applied to the mucosal surface. The proportion of solution to the treated surface should approximate 0.1 to 1.0 ml per square centimeter of mucosal surface. The vehicle would be similar to the vehicle described above for the bacteria.

In some embodiments, the invention provides a method of contraception, said method comprising the steps of contacting cells of the female genital tract with engineered bacteria as herein described. In some embodiments, according to this aspect, the method comprises administering a composition comprising the engineered bacteria to the genital tract of a female subject in need thereof, including in some embodiments, a composition as herein described. In some embodiments, the invention also provides for contacting the female genital tract with a bacteriophage as herein described, which in turn leads to engineering of the commensal flora in situ, in order to obtain the engineered bacteria as herein described.

In some embodiments, the term "contacting" or "administering" refers to both direct and indirect exposure to the indicated material.

In some embodiments, the dosage administered to the female genital tract may range from $10^5$-$10^9$ recombinant bacteria. In some embodiments, dosage is optimized for a particular host or population. In some embodiments, such optimal dosage may range from $10^7$-$10^9$ recombinant bacteria, or $10^6$-$10^8$ recombinant bacteria, or $10^8$-$10^9$ recombinant bacteria.

Various means of demonstrating effective contraception are known in the art, all of which are to be considered to be useful in this invention, some of which are exemplified herein.

In one embodiment, the contraceptive effect of the biologic contraceptive of the present invention is determined by evaluating the number of offspring produced per breeding cycle by a female animal to which was admininstered a contraceptive of the present invention. For example, following 1 to 3 days of administration of the biologic contraceptive to, for example, a mouse, individual female mice are placed in cages with a male mouse. Male mice are then removed after between 1 and 7 days post mating. Female mice are then observed daily for birth of pups. The contraceptive effect of the administered contraceptive is determined by the reduction in pregnancy and/or in the reduction in litter size following administration. For example, for animal species which produce average litters of 3 offspring or more (for example, as exemplified hereinunder, in mice the average litter size is 11 or more offspring, when outbred strains were used), the contraceptive protein can be considered effective if there is a reduction in pregnancy rate or litter size by 10%-100%, 30%-100%, or 50% to 100%, or 60%-100%, 70%-100%, or 80% to 100%, or 90%-100%, or 95%-100%, or more. As exemplified herein, when evaluating the contraceptive efficacy of a J102 expressing *L. jensenii* strain, a contraceptive efficacy of at least 50% was observed, and moreover, since colonization studies conducted herein indicated that approximately 50% of the mice were colonized well with the *lactobacilli*, it is expected therefore, that other animals known to be more receptive to *lactobacilli* colonization would have a higher contraception effect.

A contraceptive is considered effective if there is a reduction in litter size by at least 50%, and therefore, FIG. 7 demonstrates the production of an effective biologic female contraceptive, which comprises an engineered commensal, expressing an anti-sperm agent.

In some embodiments, the effectiveness of the contraceptives of the present invention may be determined by measuring the levels of expressed antibodies in mucosal secretions. The effectiveness of the contraceptive may also be evaluated by visualizing antibodies bound to the sperm by immunohistochemical techniques, for example in secretions collected post-coitus.

As exemplified herein, when mice were colonized with *L. jensenii* expressing an anti-sperm scFv, a reduction of between 50-58% was seen in the pregnancy rate and a concurrent reduction in the number of progeny produced per cage and thereby per mouse was evident, as well.

In one embodiment, the commensal organism expressing an anti-sperm agent may be further engineered to express an agent, which agent is effective against infection of the treated female with a sexually transmitted disease-causing organism. In one embodiment, the sexually transmitted disease-causing organism is Chlamydia, HIV, HPV, and others, as will be appreciated by the skilled artisan.

In one embodiment, such agent, which agent is effective against infection of the treated female with a sexually transmitted disease-causing organism may interfere with infection by the organism, or in another embodiment, such agent may reduce the incidence or load of infection. In some embodiments, such agent may interfere with the pathogenesis of infection by the organism. It is to be understood that the further incorporation of any agent which is effective against infection of the treated female with a sexually transmitted disease-causing organism is envisaged in this connection and is to be considered as part of this invention.

According to this aspect, and in some embodiments, the contraceptives of this invention may be viewed as a combinatorial contraceptive-anti-STD therapy.

While it is contemplated that the engineered commensals of this invention may be further engineered, for example to express an anti-chlaymdia scFv, or an anti-HPV or anti-HIV scFv, or other anti-HIV agents, for example, cyanovirin, it is understood that the presence of wild type *lactobacilli* colonization of the female reproductive tract is protective against STD infection. It is also contemplated, that the engineered organisms of this invention expressing an anti-sperm agent are as effective, or in some embodiments, more effective in reducing the incidence of a sexually transmitted disease in a population of females making use of such organisms as herein described than wild type *lactobacilli* alone.

It is to be understood that any embodiment described herein, as applicable to any or all methods of this invention, is to be considered as part of this invention. All publications and patent applications cited in this specification are herein incorporated by reference as if each individual publication or patent application were specifically and individually indicated to be incorporated by reference.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

It will be appreciated that reference to articles herein such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

The following are meant to provide materials, methods, and examples for illustrative purposes as a means of practicing/executing the present invention, and are not intended to be limiting.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Vplumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Preparation of Anti-Human Sperm Antibodies

Monoclonal antibodies are prepared against human sperm antigens by fusing P3-X63-Ag8-653 mouse myeloma cells with lymphocytes from Balb/c mice immunized with Tergitol NP-40 detergent-solubilized human epididymal sperm. Ascites fluid from mice injected with these hybridomas is tested for being acrosome positive on methanol fixed sperm and plasma membrane positive on unfixed sperm in indirect immunofluorescence. Antibody cross-reactivity with murine and rabbit sperm is verified.

A fertilization antigen, FA-1, is purified from either deoxycholate- or lithium diiodosalicylate-solubilized murine testes by immunoaffinity chromatography using a monoclonal antibody, MA-24, as described (Naz, R. K. et al., Proc Natl Acad Sci USA. (1986) 83(15):5713-7). Additional monoclonal antibodies to FA-1 are prepared as above, and cross-reactivity with human and rabbit sperm is verified as well.

Example 2

Cloning of Anti-Human Sperm Antibodies

RNA Preparation:

Hybridoma cells secreting antibodies which are spermicidal or diminished spermatid motility are selected. The cells are grown and counted such that 10 million cells are processed for RNA collection utilizing the FastTrack 2.0 kit (Invitrogen). Total RNA is directly isolated from the cells using a detergent lysis and protein degradation buffer. Poly (A)+RNA is then isolated using a modified Aviv and Leder protocol in which the mRNA is bound to oligo dT resin. The resin is then washed with a low salt buffer to remove extraneous total RNA, and the poly(A)+RNA is eluted from the resin. Spectrophotometric analysis at 260 nm and 280 nm indicates the final concentration of poly(A)+RNA.

Reverse Transcription and Amplification of Poly(A)+RNA

The epitope-recognizing regions or complimentary determining regions (CDRs) of the antibody are identified and oligonucleotides probing Ig heavy chain and light (kappa) chain subunits are designed.

Heavy chain oligos are obtained from the Ig-Prime kit (Novagen), and diluted to a final concentration of 1.0 µg/µl with dH$_2$O.

Reverse transcription and polymerase chain reaction amplification of respective hybridoma poly(A)+RNA are performed in a single reaction using the Access RT-PCR system from Promega. Briefly, 5 µg of hybridoma poly(A)+RNA, 1 µg of each appropriate primer (primers 1 and 2 for the heavy chain, primers 3 and 4 for the light chain), 1 µl 10 mM dNTP mix, 10 µl of 5×AMV reverse transcription buffer, 2 µl 25 mM MgSO4, 1 µl AMV reverse transcriptase, 1 µl Tfl polymerase, and 30 µl nuclease-free dH$_2$O are combined in a 0.5 ml microfuge tube. PCR reaction is conducted according to standard protocols and cycle temperatures and times are optimized. Amplified products are analyzed on an agarose gel, and gel purified.

Antibody Cloning and Sequencing:

Gel purified products are subcloned into an appropriate vector, which produces high yields of the products. Vector, buffer, cDNA and T4 DNA ligase are incubated at room temperature for 1 hour, and then heated at 65° C. for 10 minutes. Supercometent E. coli cells are utilized, and DNA is added to the cells and incubated on ice, then heated at 42° C., and SOC media is added. Cell are then incubated in a 37° C. shaking water bath for 1 hour. These cells were then spread on LB containing selection compound petri dishes and incubated overnight at 37° C. Positive colonies are chosen and grown for plasmid purification.

Plasmids are purified using Qiagen-tip 20 columns according to manufacturer's instructions.

To confirm the presence of a cDNA insert in the purified plasmids each clone is digested with the appropriate restriction enzymes, and digested products are run on an agarose gel. Clones containing the insert are sequenced.

Sequence Analysis of Heavy and Light Chain Clones

Positive clones are sequenced using the Fidelity kit (Oncor), according to manufacturer's instructions. Sequencing reactions consist of plasmid DNA, primer (e.g. T3 primer, which lies upstream of the 5' cloning site on the pCR-Script vector), and dH$_2$O, which are heated to 95° C. for 5 minutes, annealing buffer is added, and the reactions are incubated at 37° C. for 15 minutes. The reactions are labelled by the addition reaction buffer, $^{33}$PαATP, T4 DNA polymerase, and dH$_2$O and incubated at 400° C. for 15 minutes, then A, C, G, or T termination mix is added and incubated at 40° C. for 5 minutes. The reactions are stopped by the addition of Proteinase K solution and heated to 95° C. prior to loading on an acrylamide sequencing gel. The gel is then run for 2 hours at 2000 volts, dried onto Whatman 3 MM filter paper under vacuum, and exposed to x-ray film overnight at room temperature. After development of the film the gels are read on a lightbox.

Sequencing may also be conducted using an Automated DNA Sequencer (e.g. ABI Prism 377). For each clone, cDNA and primer are combined with four dye-labeled dideoxy nucleotides and AmpliTaq polymerase FS. The entire reaction is loaded in a single lane for electrophoresis on a 36 cm well-to-read 5.0% acrylamide gel. Real time detection of the electrophoresed individual fragments is achieved with laser scanning with CCD camera imaging production.

Construction of Expression Vector

Expression vectors as described in McCracken A., et al. (2000) Arch. Microbial. 173: 383-389; Perez-Casal, j., et al. (2003) Mol. Microbiol. 8: 809-819; Kruger C. et al. (2002) Nature Biotechnology 20: 702-706; Rao, S. et. al., (2005) PNAS 102: 11993-11998; Liu X. et. al. (2006) Antimicrobial Agents and Chemotherapy 50: 3250-3259; del Rio B. et. al. (2008) Clinical and Vaccine Immunology 15: 1429-1435; U.S. Pat. No. 7,312,076, or European Patent No. 1 011 721 B1 will be obtained or variations thereof will be prepared by methods known in the art.

Alternatively, a vector will be constructed as follows:

A shuttle vector is created by subcloning the E. coli origin of replication from pBluescript into the backbone vector (Fons, M., et al. (1997) Plasmid 37, 199-203), and then removing the full-length M6 coding region (PstI). This plasmid is digested with SmaI, partially digested with NdeI, filled-in by DNA polymerase I (Klenow fragment) and self-ligated. The resulting plasmid contains a lactobacillus-compatible origin of replication (repA) and a positive selectable marker, e.g. an antibtiotic resistance gene, and has been used for the expression of heterologous proteins in a variety of lactobacillus species.

Cloning of the Amplified Antibody Fragments into a Vector

Amplified products corresponding to the heavy and light chain are gel purified and resuspended in dH$_2$O. The antibody may be recoded by assembly PCR (Stemmer W. P. et al, (1995) Gene 164: 49-53) to conform more closely to the optimal lactobacillus codon usage.

An expression cassette is constructed by PCR amplification and subcloned into the appropriate sites of the vector. The cassette contains four components, including lactobacillus-compatible promoter elements, antibody fragment, signal sequence for secretion or cell wall anchoring domain. Unique restriction sites are placed between each component from 5' to 3' ends, respectively. Amplification of each component by PCR is performed by using Pfu DNA polymerase. The P23 promoter from Lactococcus lactis (van der Vossen, J. M., et al. (1987) Appl. Environ. Microbiol. 53, 2452-2457) is created by amplification with 5'-GTGGAGCTC-CCCGAAAAGCCCTGACAACCC-3' and 5'-GGAAA-CACGCTAGCACTAACTTCATT-3' primers. To direct secretion of the antibody, primers are designed to amplify the S-layer gene (cbsA) sequence of L. crispatus from the putative ribosome binding site to the signal peptidase cleavage site, with unique sites added to the 5' and 3' ends, respectively. The amplified S-layer signal nucleotide sequence (CbsAss) corresponding to MKKNLRIVSAAAAALLAVAPVAA is then digested and used for cloning in the expression cassette.

Products are ligated into the vector, and a TAA stop codon is inserted to the N-terminal anchoring motif to ensure secretion. Sequence verification is conducted prior to transformation into *lactobacilli* strains.

Lactobacilli Transformation:

Bacterial Strains and Culture. Naturally occurring human vaginal isolates of *L. crispatus, L. gasseri*, and *L. jensenii*, and others may be obtained from vaginal swabs of healthy volunteers or alternatively, commercially available strains may be utilized and cultivated at 37° C. (5% $CO_2$/95% air) in either de Man, Rogosa, and Sharpe (MRS) broth or Rogosa SL broth (Difco). For protein expression analysis, Medium 199 (Invitrogen) is also used. Plasmids are introduced by electroporation into *Escherichia coli* DH12S (Invitrogen). For plasmid maintenance, the transformed *E. coli* DH12S are grown in LB broth (Difco) at 37° C., supplemented with erythromycin (300 μg/ml). Plasmids are transformed by electroporation into *L. jensenii* essentially as described for *L. gasseri* (Luchansky, J. B., Tennant, M. C. &Klaenhammer, T. R. (1991) J. Dairy Sci. 74, 3293-3302). The transformed *L. jensenii* bacteria are routinely propagated in liquid media containing 20 μg/ml erythromycin.

Engineered *lactobacilli* are probed for anti-sperm activity as described hereinbelow.

Example 3

Generation of a Series of Anti-Sperm scFv

Library Construction

A human scFv filamentous phage display library for isolating human VH-VL tethered variable domians against the sperm proteins was utilized. The human scFv library was prepared using primers designed according to the sequences obtained at V Base (http://vbase.mrc-cpe.cam.ac.uk) and according to techniques described previously by Barbas & Lerner (Barbas, Bain et al. 1992 Proc Natl Acad Sci USA 89(10): 4457-61; Gram, Marconi et al. 1992 Proc Natl Acad Sci USA 89(8): 3576-80; Zebedee, Barbas et al. 1992 Proc Natl Acad Sci USA 89(8): 3175-9; Barbas, Amberg et al. 1993 Gene 137(1): 57-62), Winter (Hawkins, Russell et al. 1992 J Mol Biol 226(3): 889-96; Hawkins and Winter 1992 Eur J Immunol 22(3): 867-70; Hoogenboom, Marks et al. 1992 Immunol Rev 130: 41-68; Hoogenboom and Winter 1992 Immunol Rev 130: 41-68; Marks, Griffiths et al. 1992 Biotechnology (N Y) 10(7): 779-83; Marks, Hoogenboom et al. 1992 J Biol Chem 267(23): 16007-10; Marks and Winter 1992 Behring Inst Mitt(91): 6-12; Orlandi, Gussow et al. 1992 Biotechnology 24: 527-31; Tomlinson, Walter et al. 1992 J Mol Biol 227(3): 776-98) and by the Benhar laboratory (Azriel-Rosenfeld, Valensi et al. 2004 J Mol Biol 335(1): 177-92). Amplification of antibody genes by PCR was performed using human spleen and peripheral blood lymphocyte cDNA as a templates. In this library, the repertoire of human heavy and light chain variable domains, are tethered together in combinatorial fashion to create all possible combinations of VH-VL artificial binding molecules that are fused to the p3 gene of the m13 filamentous phage, and the fusion protein is then displayed on the phage surface in typically a single copy per phage on average.

Sperm Antigens

Peptides were designed from sperm antigens FA-1 and YLP(12) respectively. Peptide 1 below is a 35 residue peptide designed from antigen FA-1 and peptide 2 below is the YLP (12) peptide. The peptides were biotinylated for ease of binding to magnetic beads for the protocol outlined below. Peptide 2 has the addition of a tether between the biotin and peptide as the peptide sequence is relatively short. The phage display scFv library was screened against both peptides as outlined below.

Antibody Screening

Library stock was grown in LB+Amp (100 ug\ml)+1% glucose at 37° C. Helper phage M13KO7 was added, and cultures were incubated with the helper phage in the presence of 100 ug\ml Amp+30 ug\ml kan overnight at 30° C. Cultures were spun at 4000 RPM for 10 minutes, and the supernatant filtered through a 0.45 micron filter and 1\5 volume PEG\NaCl was added, and the filtrate was placed on ice for a minimum of one hour, then spun for 30 minutes at 4000 RPM, after which the phage-containing pellet was suspended in PBS. Phage blocking with 4% BSA for 30 minutes at a minimum was conducted, and magnetic-bead based antibody selection was accomplished according to the protocol as described in R. Kontermann and S. Dubel (eds.), Antibody Engineering Vol. 1, Springer-Verlag Berlin Heidelberg 2010, pages 267-287. Blocking was conducted for a minimum of 30 minutes with 2% BSA. Blocked beads were added to the blocked phage, and bead removal, which thereby removes all phage that bind strepavidin. Blocked phage was then incubated with biotin for 30 minutes subsequently incubated with the beads for 30 minutes, after which the beads were discarded.

Phage were then incubated with the following peptides for one hour:

ACGVSRPVIACSVTIKEGSQLKQQIQSIQQSIERL (SEQ ID NO: 1) - - - Biotin; and YLPVGGLRRIGG (SEQ ID NO: 2) - - - Ahx - - - and then incubated with the beads for 30 minutes, washed and eluted. Neutralized eluate was then mixed with dh5α F+ cells for 60 minutes at 37° C. and cultured on LB+ 100 ug\ml Amp+ 1% glucose plates over night. The panning steps were repeated for a number of cycles.

Antibody Fragment Specificity

An ELISA assay was conducted using the peptides as probes and the fragment relative affinity was assessed by O.D.

Infected *E. coli* TG-1 with panning output phages (as described above) were plated to yield individual colonies. These colonies were picked into 100 μl YTAG media in wells of a flat bottom sterile 96-well plate and grown at 30° C. shaker at 150 RPM ON. 10 μl of phage were transferred into a fresh 96-well plate containing 90 μl of YTAG+2.5 μl/ml ($5 \times 10^8$ CFU) of M13KO7 helper phage and grown at 37° C. without shaking for 30 min following shaking at 150 RPM for 30 minutes. Plates were centrifuged at 4000 RPM for 5 minutes at 14° C. and the supernatant was discarded. 200 μl/well of YTAK (with Kanamycin) was added and the plate was left to grow at 30° C. shaker at 150 RPM overnight. The bacteria plate was then centrifuged at 4000 RPM for 5 minutes at 4° C. and 100 μl of the supernatant mixed with 100 μl of PBST was used for the ELISA.

100 μl/well of antigen and control antigen were plated in ELISA plates at 4° C. overnight to coat the plates. The ELISA plates were washed once with washing buffer (300 μl/well of PBST) and blocked with 3% milk/PBS for 1 hr at room temperature (RT). Plates were washed once with washing buffer. The phages were then added to the plates and incubated for 1 hour at RT following 3 washes with washing bafferbuffer. 50-100 μl/well of HRP conjugated anti phage diluted anti-M13 phage antibody were added and incubated for 1 hour at RT. After 3 washes with washing buffer 100 μl/well of OPD substrate solution were added for 20 minutes at RT. The reaction was then stopped with 50 ml of 1 M HCL solution plates were read plates at 450 nM. Detection was achieved using a horseradish peroxidase (HRP)-tagged anti-phage antibody and the color resulting from the substrate-enzyme reaction was read with an automated ELISA reader.

Another ELISA protocol coating the plates with 2 μg/ml of BSA-biotin in PBS for 2 hours at room temperature. Plates were washed with PBST and subsequently coated with 2 μg/ml streptavidin in PBS for 2 hours at room temperature, and washed again with PBST. Plates were then coated with 2 μg/ml of a peptide in PBS overnight at 4° C., washed once with PBST and blocked with a 3% solution of milk/PBS for 1 hour at 37° C., with the remainder of the protocol being the same as above except that plates were developed with 50 μl/well of TMB TMB (Tetramethyl benzidine) Stop Reagent diluted four times in SDDW and stopped after 5 minutes with 50 μl/well of 1M $H_2SO_4$.

Results

Figure 2:
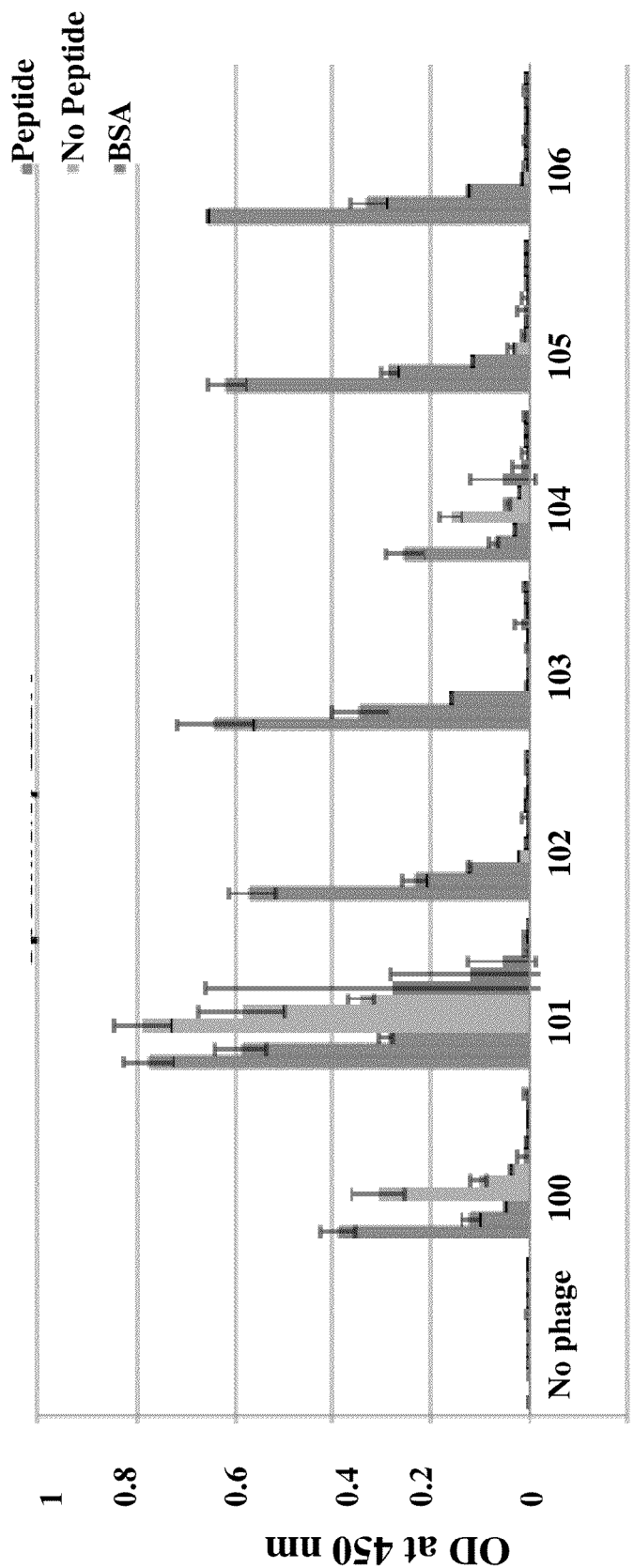
FIG. 2 depicts the relative affinities of some phage-displayed scFvs isolated and cloned for the probed sperm peptides. Clones were considered to have high affinity when the OD value was higher in relation to peptide versus BSA controls, or in samples incubated without peptides. Clones 102, 103, 105 and 106 in particular, showed relatively high affinity for the peptide and Clone 102 was further characterized in vitro and in vivo.
Figure 3:
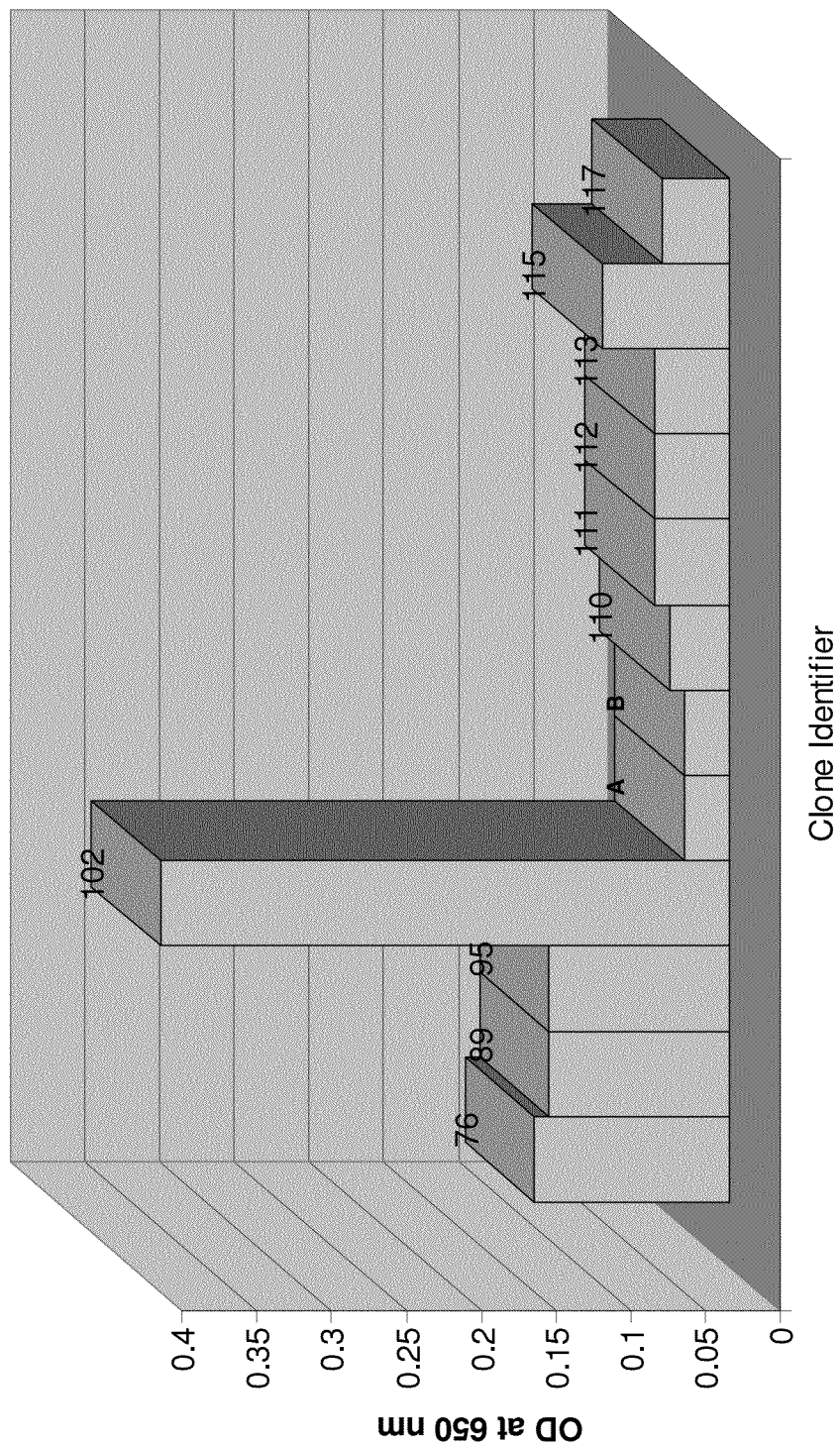
FIG. 3 graphically depicts the results of ELISA binding assays identifying a series of non-binding scFv, which were then utilized as controls, as compared to Clone 102, which as shown in FIG. 2 was found to have good affinity for the probed peptides. One such scFv clone, J112, was typically utilized in this context. Controls A and B, which were samples containing no scFv phage, or no peptide and no scFv, respectively, were assessed, as well. Binding was detected by measuring the OD in samples probed with anti-phage HRP labeled antibody (antibody to PVIII).

FIG. 1 graphically depicts the relative affinities of the phage-displayed scFvs isolated and cloned for the probed sperm peptides. Columns 1-3 represent binding of three scFvs to the FA-1 derived peptide and columns 4-6 represent binding of three scFvs to the YLP(12) derived peptide. BSA is used as a negative binding control. The scFvs exhibited significant affinity for the indicated peptides in compari$_s$on to controls. FIG. 2 depicts the relative affinities of some phage-displayed scFvs isolated and cloned for the probed sperm peptides. FIG. 3 shows the results of ELISA binding assays identifying a series of non-binding scFv, which were then utilized as controls. One such scFv clone, J112, was typically utilized in this context. Clone J102 showed greater affinity than other clones and controls A and B, which were samples containing no scFv phage, or no peptide and no scFv, respectively. Binding was detected by measuring the OD in samples probed with anti-phage HRP labeled antibody (antibody to PVIII). Some of these scFvs were subsequently utilized in Examples hereinbelow, serving as controls and contraceptives, as appropriate.

Example 4

Engineered *Lactobacilli* Expressing scFv

Figure 4A:
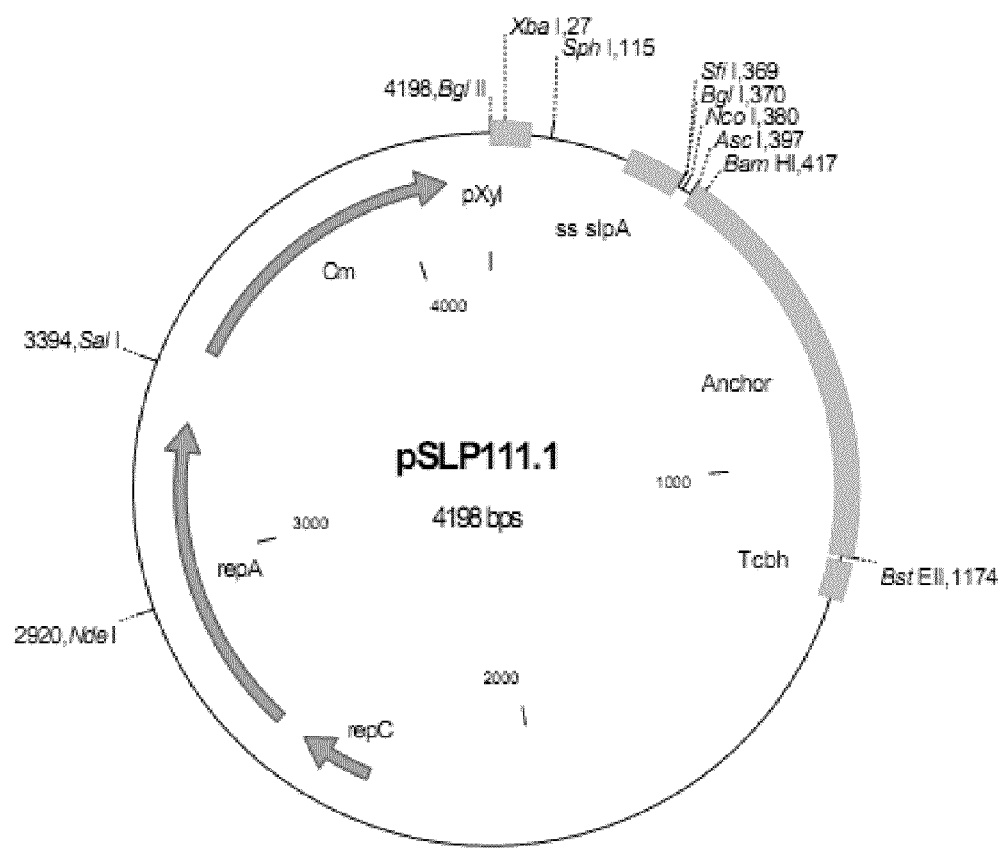
FIG. 4A is a plasmid map of the pSLP111.1 vector.

Antibody Cloning and Sequencing:

scFv were released from the phagemid genome by digestion with NcoI and NotI cleavage according to established protocols to demonstrate intact scFv fragments in the phage clones. Gel purified products were subcloned into the pSLP111.1 vector, a kind gift from Dr. Jos Seegers, which produces high yields of the products. A map of the vector is provided in FIG. 4A. Subcloning was performed by PCR amplification of the scFv with unique primers that contained on the 5' primer a NcoI restriction site and on the 3' primer an AscI site (5'-GCGCCATGGCCGAGGTGCAGCTGTTG, 3'-GCGGGCGCGCCCCAGCACAGTGAGTTTG-GTCCC). The amplified DNA was gel purified and the restriction sites activated by cleavage with NcoI and AscI. The restricted DNA fragment was then gel purified a second time and the ligated into (with T4 ligase) the PSLP111.1 vector that was previously cut with NcoI and AscI and gel purified too. The ligation mix was transformed with *E. coli* DH5alpha that were made competent by the calcium chloride technique (Maniatis). Transformed bacteria were plated onto LB agar chloramphenicol plates (10 micrograms/mL), colonies picked after overnight incubation and plasmid DNA was prepared from two dozen colonies. The plasmid DNA was prepared from these colonies using a Qiagen miniprep plasmid kit and cut with NcoI and AscI to identify those containing the appropriate sized DNA insert. Positive clones were then moved into *Lactobacillus jensenii* as described hereinbelow.

Plasmids were purified using Qiagen-tip 20 columns according to manufacturer's instructions.

To confirm the presence of a cDNA insert in the purified plasmids each clone was digested with NcoI-AscI, and digested products were run on an agarose gel. Clones containing the insert were sequenced.

Sequence Analysis of Heavy and Light Chain Clones

Positive clones were sequenced by the sequencing service of the Weizman institute, which used an ABI automated sequencer with all conditions and reagents according to manufacturers instructions. Initial sequencing primers used were:

```
                                       (SEQ ID NO: 9])
Forward CCATGATTACGCCAAGCTTGGGAGCC (SEQ ID NO: 10)
Reverse GAATTCAACCTTCAAATTGCC
```

Cloning of the Amplified Antibody Fragments into a Vector

Gel purified amplified products were subcloned into the appropriate sites of the vector. The cassette contains four components, including *lactobacillus*-compatible promoter elements, antibody fragment, signal sequence for secretion or cell wall anchoring domain.

Sequence verification was conducted prior to transformation into *lactobacilli* strains.

*Lactobacilli* Transformation:

The ATCC human vaginal isolate of *L. jensenii* strain number 25258 was utilized and cultivated at 37° C. (5% $CO_2$/95% air) in de Man, Rogosa, and Sharpe (MRS) broth (Difco). pSLP111.1 containing the insert were introduced by the calcium chloride technique into *L. jensenii*. The transformed *L. jensenii* bacteria were routinely propagated in liquid media containing 10 μg/ml chlormaphenicol.

Sperm Binding and Motility Assays:

Mouse sperm was isolated according to established protocols [Liu Z, et al., Journal of Biological Chemistry (2010) 285, 2758-2770.]. $10^6$ sperm were suspended in sperm buffer (Ham's F-10 supplemented with 21 mM HEPES; 4 mM Sodium bicarbonate; 0.6% Human serum albumin; 3.6 ml Sodium lactate (60% stock) and Gentamicin: 10 microgram/ml) in conical tubes, sperm were maintained in a manner facilitating their ability to swim up to the top portion of the tube, where collection of motile sperm was accomplished by removal of a small volume (a few hundred microliters) of buffer. Sperm count was verified via hemactometer and inclubated at a ratio of 1:1 or 1:2, sperm: *Lactobacilli* (cfu).

Mouse sperm was isolated and scFv binding to sperm was assessed by binding assays utilizing phage-displayed scFv. A swim up assay as described above was utilized for selecting motile sperm, which were isolated and placed in chamber slides, airdried, and then phage-containing the scFvs of interest ($10^8$) were applied to the chambers, and incubated for 1 hour, washed, then sperm was probed with anti-cp8 antibody linked to HRP (ENCO, Israel), at a dilution of 1:200, chambers were then washed, and developed with DAB and peroxide.

Results

Figure 4B:
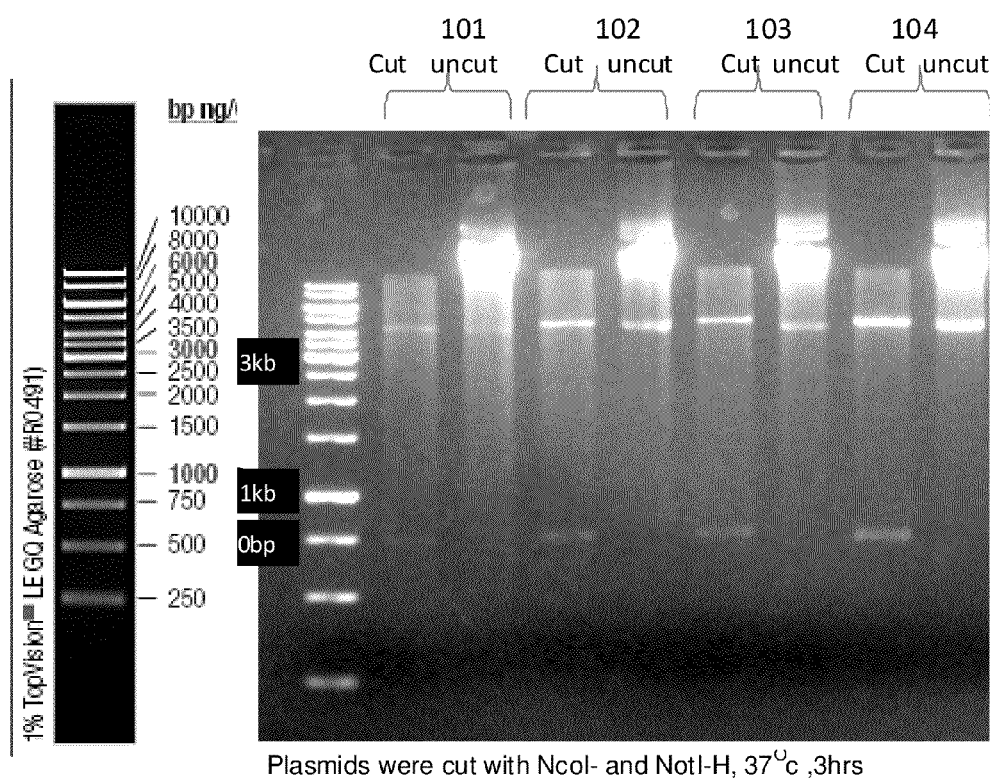
FIG. 4B is a photograph depicting the plasmid NcoI and NotI digestion products. The plasmids were cut with NcoI- and NotI, at 37° C. for three hours. The plasmid insert is clearly shown in several representative clones.

FIG. 4B shows plasmid NcoI and NotI digestion products. The plasmids were cut with NcoI- and NotI, at 37° C. for three hours.

One embodied scFv, J102, was found to have a high binding affinity to the highly conserved sperm antigen. Sequencing of the clone yielded a complete DNA and protein sequence as shown in FIGS. 5A-5B (SEQ ID NO: 7-8).

The scFv J102, and others, were probed for binding to both human and murine sperm. Although the scFv J102 is a human-derived fragment, the high conservation among species of the FA-1 antigen resulted in the J102 binding to both murine and human sperm, as determined in in vitro assays. FIG. 6A shows significant binding of the *lactobacilli* expressing scFv to mouse sperm, with almost each sperm cell evaluated showing significant staining, whereas control *lactobacilli* expressing scFv to non-sperm antigen did not appreciably bind to murine sperm (FIG. 6B). Human sperm binding studies were consistent with mouse findings (data not shown).

Motility studies were conducted with human sperm, as described in the methods section hereinabove. Whereas *lactobacilli* expressing an irrelevant control showed a modest effect on sperm motility in vitro, when *lactobacilli* expressing sperm-binding scFv were utilized, a pronounced effect was seen impairing sperm motility, including in assays probing for the effect of scFv J102, and motility was found to be decreased by 50% in comparison controls, indicating a potential for the *lactobacilli* expressing sperm-binding scFv to interfere with sperm function.

Example 5

Anti-Sperm Activity of Engineered *L. jensenii*

Inhibition of Fertilization:

$10^5$ sperm of respective species are incubated overnight in the cold in solutions of relevant and control antibody (diluted 1:50, 1:5 or 1:1), or constructs producing control and relevant antibody, and eggs are added, at which point the binding of sperm to egg is allowed to proceed for one hour. The eggs are then washed, and the number of sperm bound per egg is determined, and expressed as a percentage of that bound to control samples. Constructs with greatest percent inhibition are further evaluated.

In Vivo Fertilization Inhibition Studies:

Females (mice, rabbits) are injected intravaginally with purified relevant antibody fragments, purified control antibody fragments, engineered *lactobacilli* expressing the relevant antibody fragments, and engineered *lactobacilli* expressing the control antibody fragments. One male and 2-4 females are housed at multiple points post intravaginal administration to females of the respective agents. 24 hours after the grouping, females are checked visually daily for presence of vaginal plugs. Females are marked to be distinguished therebetween (for example by successive ear punches) and optionally, two weeks after the initiation of the mating the, females are removed into individual cages. After three weeks, pregnant females having litters and progeny are counted. Constructs with the greatest contraceptive activity may then be selected and further evaluated/optimized.

Fusion inhibition assays are carried out as follows. Young female mice (8-10 weeks of age) are injected with 5 units of pregnant mare's serum (PMS) in 0.9 NaCl intraperitoneally. 48 hours later, the mice are injected IP with 5 units of hCG (human chorionic gonadotrophin) in 0.9% NaCl to trigger super ovulation. 14-16 hours after hCG injection, the ovulated oocytes are collected and treated with hyaluronidase to remove cumulus cells. The zona pellucida is removed with a mixture of proteases. The zona pellucida free eggs are incubated in culture media with peptide at a specified concentration for 30 minutes [Hogan, B., et al., Manipulating The Mouse Embryo, 91-101, (1986)]. Sperm collected from the epididymis of male mice is capacitated by incubation and acrosome reacted as described by Fleming and Yanagimachi [Gamete Res. 4, 253-273 (1981)] and added to the eggs, in the presence of control and relevant antibody, and constructs expressing the same, and incubated for 15 minutes. The eggs are then transferred to a sperm free culture medium and incubated for an additional 1 hour and 45 minutes. The eggs are then fixed and stained as described by Primakoff et al., [J. Cell. Biol. 104, 141 (1987)]. The total number of swollen sperm heads are then counted. Swollen sperm heads are an indication that the sperm and egg have fused.

On the basis of these observations, several indices are calculated. The fertilization index (F.I.) is determined by dividing the total number of swollen heads by the total number of eggs. The fertilization rate (F.R.) is the percentage of eggs fertilized. The percent inhibition is determined by dividing the fertilization index of the experimental peptide by the fertilization index of the control peptide. Constructs with the greatest activity are selected.

Example 6

Engineered *L. jensenii* as Effective Contraceptives

Other animal species will be probed according to the methods described in Example 4. Rabbits, rats, guinea pigs, minipigs, monkeys and other species may be evaluated. Several constructs will be evaluated in this context, and animal species differences noted. A percent efficacy will be determined for each construct, in each animal strain.

In addition, each species will be subjected to AIF with semen obtained from males of proven fertility, where sperm count and motility are assessed. *Lactobacilli* expressing relevant and control antibody fragments are applied intravaginally and AIF is performed at varied times post administration. At the time of artificial insemination, ovulation is induced by an injection of e.g. 100 IU of hCG. After ovulation and artificial insemination, females are allowed to complete their pregnancy to assess potential teratogenic effects.

Females administered *lactobacilli* control and *lactobacilli* expressing relevant antibody fragments will be evaluated for persistence in the genital tract.

Toward this end, vaginal secretions are collected by repeatedly pipetting sterile PBS into the vaginal opening. The fluid and mucus are mixed spun down briefly in a microfuge, and the supernatant fluid is assayed for presence of the scFv. Anti-sperm antibody fragment titers in the serum and vaginal washings are determined by an ELISA.

Time course studies are conducted. Females administered the *lactobacilli*, are repeatedly housed with males, and pregnancy rate/contraceptive efficacy assessed, as a function of time post-administration.

Example 7

*L. jensenii* Expressing Sperm-Binding scFv are Effective Contraceptives in Mice Mouse Administration and Mating Studies:

Female ICR mice were anesthetized with 0.1 ml/gm weight of a solution of Ketamine (conc. 100 mg/ml) 0.5 ml Xylazine (conc. 20 mg/ml) and 8.5 ml Normal saline 0.9%. Anesthetized mice were then intravaginally administered $10^8$ freshly grown mid-log phase of engineered *L. jensenii* (determined by OD) J102 or control J112 strains. (N=12 mice per group).

Following administration, the females were kept on their backs, pelvis tipped upward for from 30-60 minutes. *Lactobacilli* was administered to the females daily for 3 days and then were mated with age-matched ICR strain males. Males were housed with the females for 7 days, rotated between every other day during this period and then removed. Females were then assessed visually for the presence of plugs, and the number of pregnant mice and progeny produced per cage was recorded.

Mouse Colonization Studies:

Between 12 and 24 hours following a first intravaginal administration, females were swabbed or lavaged vaginally and recovered sample/fluid was plated on chloramphenicol—containing MRS plates and cultured at 37° C. for 24 hours. The presence of bacterial lawns served as indicators of vaginal colonization.

Results

Mouse colonization studies demonstrated that up to 50% of the lavage fluids yielded lawns indicating that colonization occurred in up to 50% of the mice, following a single intravaginal administration. Vaginal persistence of the administered *lactobacilli* for up to 5 days post-administration was found, in animals for which colonization was demonstrated by swabbing.

Figure 7A:
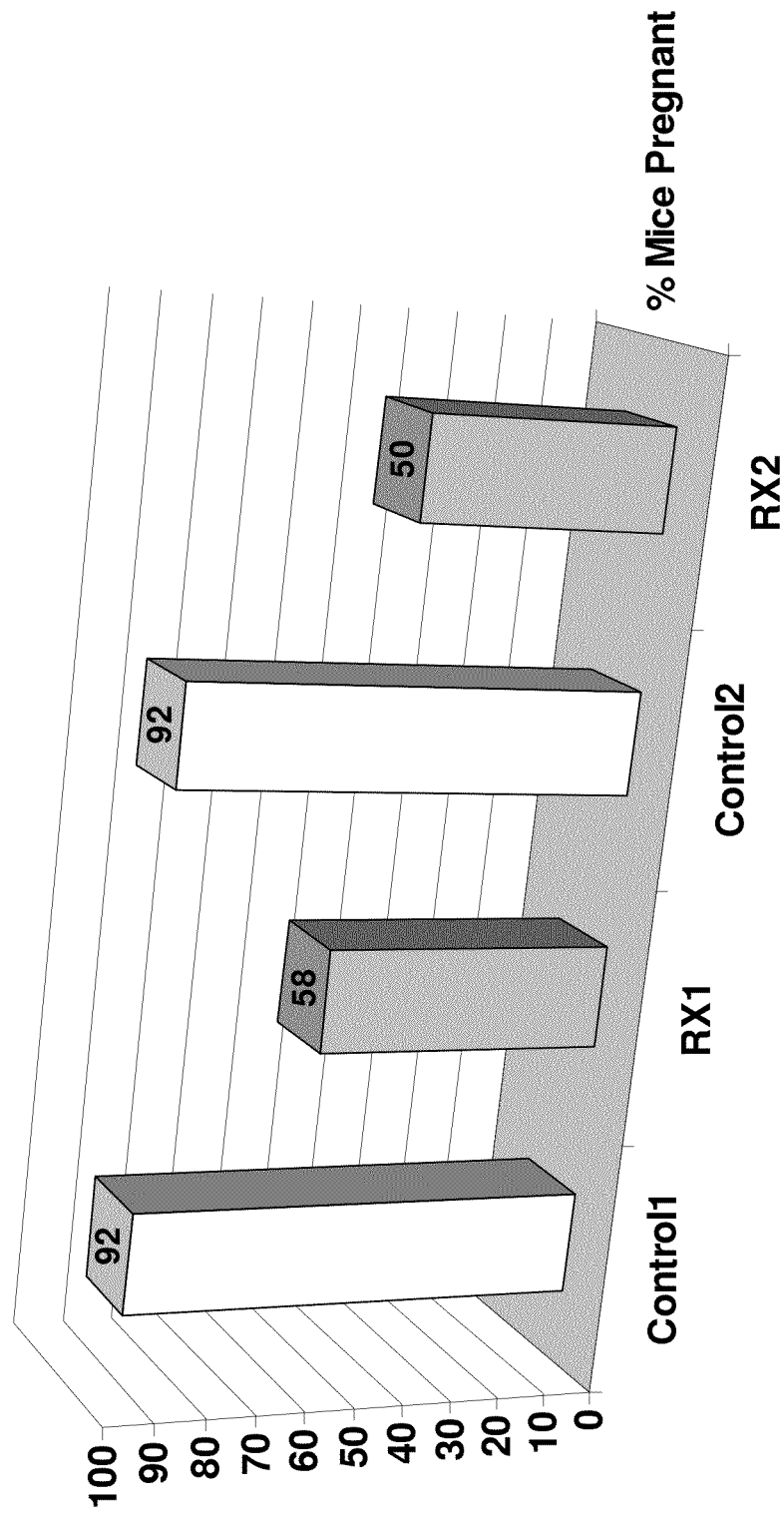
FIG. 7A plots pregnancy rates of female mice in two experiments administered the anti-sperm scFv J102 expressing *L. jensenii* or control *lactobacilli* expressing an scFv which does not bind sperm (J112), and in each experiment, effective contraception was demonstrated in J102 versus J112 treated mice.

Two individual experiments were conducted where females were administered the anti-sperm scFv expressing *L. jensenii* or control strain, and in each experiment, effective contraception was demonstrated (FIG. 7A). Whereas 92% of the control females were pregnant in each experiment, females treated with the anti-sperm scFv expressing *L. jensenii* showed a significant reduction in pregnancy rate (58% or 50%).

Figure 7B:
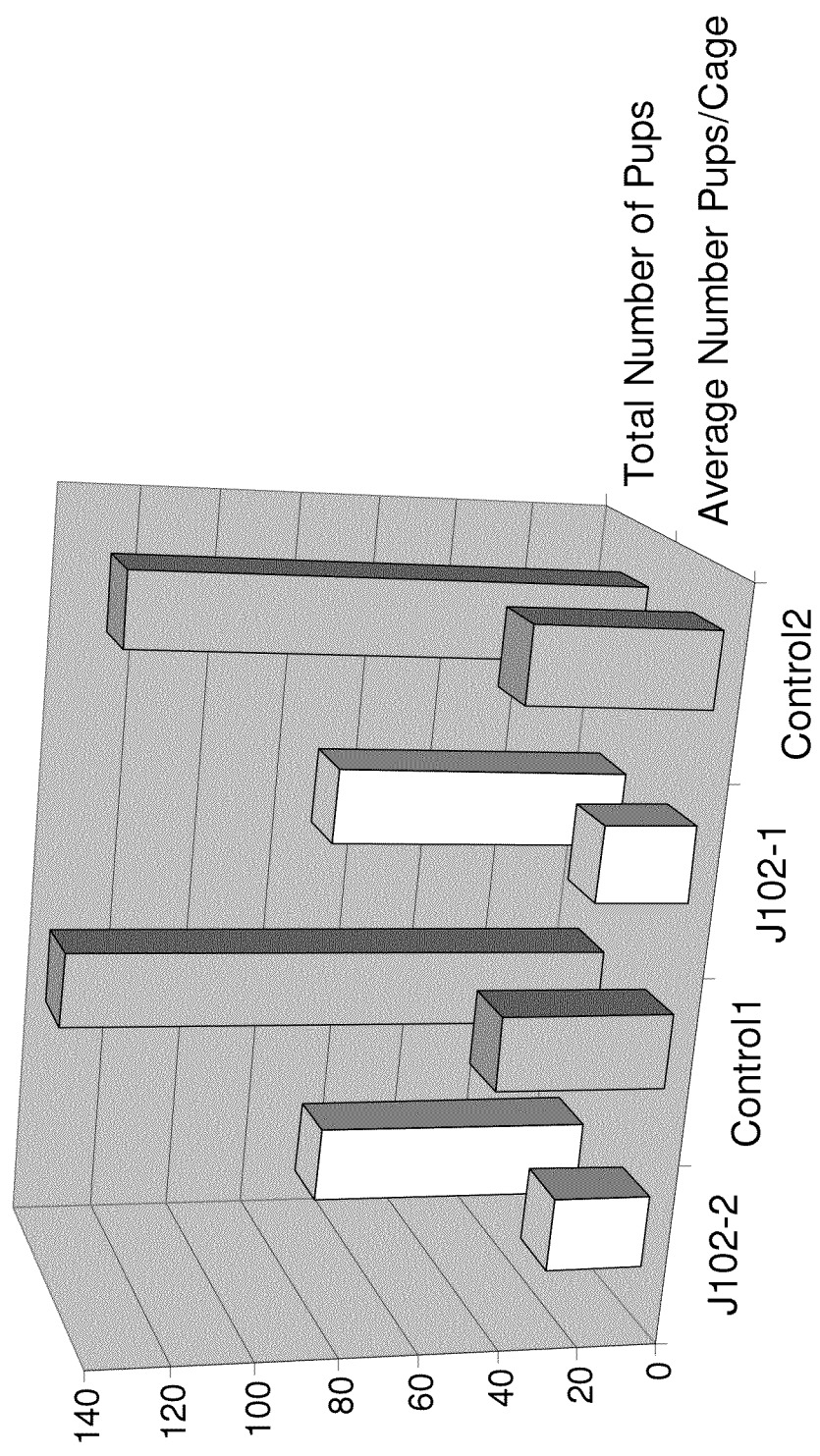
FIG. 7B plots the number of total progeny and number of progeny per cage in each of the two experiments conducted as described in FIG. 7A, and both the number of total progeny and progeny per cage were reduced in J102 expressing *L. jensenii*, in comparison to controls.

The number of total progeny and number of progeny per cage was reduced in comparison to controls, as a consequence of the administration of an anti-sperm scFv expressing *L. jensenii*, as well (FIG. 7B). Based on these findings, the number of progeny per mouse was also reduced in treated females in comparison to controls.

Example 8

Safety of the Biologic Contraceptive

Engineered *lactobacilli* are evaluated for their effect on vaginal irritability. Animals, such as mice are treated intravaginally with the *lactobacilli*, once per day for 10-30 consecutive days. Animals are then killed and the reproductive tract is examined grossly and microscopically.

Vaginal tissues are examined for epithelial ulceration, edema, leukocyte infiltration, and vascular congestion, as a function of introduction of *lactobacilli*, and engineered *lactobacilli* expressing control and relevant antibodies. The animals treated with engineered *lactobacilli* are compared to those administered natural isolates, as well as untreated animals. Improvement in genital tract histology will be noted, if existing.

Example 9

Contraceptive Reversibility

Female animals which despite repeat matings are not gravid, as a function of *lactobacilli* administration, will be administered antibiotics and mated. Pregnancy will be assessed as a measure of the reversibility of the engineered *lactobacilli*. Similarly, animals will be evaluated for persistence of the *lactobacilli* in the genital tract. Upon indication of diminished or absent population with the engineered *lactobacilli*, animals will be mated, and their gravidity determined.

Once safety and efficacy studies have been conducted in appropriate animal models, for example, as described hereinabove, then human clinical trials are contemplated, as well.

What is claimed is:

1. A genetically engineered commensal bacterium of the female genital tract, wherein said genetically engineered bacterium is a *Lactobacillus* engineered to express an anti-sperm agent.

2. The engineered bacterium of claim 1, wherein said anti-sperm agent is an scFv antibody fragment against sperm.

3. The engineered bacterium of claim 2, wherein said scFv antibody fragment against sperm is human or humanized.

4. The engineered bacterium of claim 2, wherein said scFv antibody fragment specifically interacts with the acrosome or plasma membrane.

5. The engineered bacterium of claim 2, wherein said scFv antibody fragment specifically interacts with the sperm neck region.

6. The engineered bacterium of claim 2, wherein said scFv antibody fragment specifically interacts with a sperm FA-1 antigen or a fragment thereof.

7. The engineered bacterium of claim 2, wherein said scFv antibody fragment specifically interacts with a peptide sharing at least 90% identity with SEQ ID NO: 1 or 2.

8. The engineered bacterium of claim 2, wherein said scFv antibody fragment has a sequence sharing at least 90% identity with SEQ ID NO: 8.

9. The engineered bacterium of claim 2, wherein said scFv antibody fragment is encoded by a polynucleotide having a sequence sharing at least 90% identity with SEQ ID NO: 7.

10. The engineered bacterium of claim 8, wherein said commensal bacterium is *L. jensenii*, *L. crispatus* or *L. caseii*.

11. A composition comprising the engineered bacterium of claim 1.

12. The composition of claim 11, wherein said composition is in the form of a vaginal suppository, sponge, cream or foam.

13. An intravaginally inserted device comprising the engineered bacterium of claim 1.

14. The intravaginally inserted device of claim 13, wherein said device is an intravaginally inserted ring.

15. A method of contraception, said method comprising the step of contacting cells of the genital tract of a female subject with the engineered bacterium of claim 1 in an amount effective to inhibit or prevent sperm motility, sperm-egg fusion or egg penetration in said female subject.

16. The method of contraception of claim 15, said method comprising the step of contacting cells of the genital tract of a female subject with the composition of claim 15 in an amount effective to inhibit or prevent sperm motility, sperm-egg fusion or egg penetration in said female subject.

* * * * *